United States Patent
Maiorano et al.

(10) Patent No.: US 11,547,276 B2
(45) Date of Patent: Jan. 10, 2023

(54) OPTICAL BULB FOR SURGICAL INSTRUMENT PORT

(71) Applicant: The Children's Medical Center Corporation, Boston, MA (US)

(72) Inventors: Anthony Maiorano, Waltham, MA (US); Jeffrey C. Cerier, Franklin, MA (US); Benjamin D. Masella, Burlington, MA (US); David P. Biss, Brighton, MA (US); Brian E. MacMillin, Somerville, MA (US)

(73) Assignee: The Children's Medical Center Corporation, Boston, MA (US)

( * ) Notice: Subject to any disclaimer, the term of this patent is extended or adjusted under 35 U.S.C. 154(b) by 600 days.

(21) Appl. No.: 15/916,467

(22) Filed: Mar. 9, 2018

(65) Prior Publication Data

US 2019/0274522 A1    Sep. 12, 2019

(51) Int. Cl.
| A61B 1/00 | (2006.01) |
| A61B 1/05 | (2006.01) |
| A61B 17/00 | (2006.01) |

(52) U.S. Cl.
CPC ...... *A61B 1/00096* (2013.01); *A61B 1/00126* (2013.01); *A61B 1/05* (2013.01); *A61B 17/00234* (2013.01)

(58) Field of Classification Search
CPC ... A61B 1/00096; A61B 1/00126; A61B 1/05; A61B 17/00234
See application file for complete search history.

(56) References Cited

U.S. PATENT DOCUMENTS

| 2,243,992 A | 6/1941 | Wappler |
| 2,767,705 A | 10/1956 | Moore |
| 4,201,199 A | 5/1980 | Smith |

(Continued)

FOREIGN PATENT DOCUMENTS

| EP | 1426072 A1 | 6/2004 |
| EP | 2433551 A1 | 3/2012 |

(Continued)

OTHER PUBLICATIONS

ISA, "International Search Report", PCT/US2018/021680, dated May 24, 2018.

(Continued)

*Primary Examiner* — Timothy J Neal
*Assistant Examiner* — William B Chou
(74) *Attorney, Agent, or Firm* — Fish & Richardson P.C.

(57) ABSTRACT

An optical bulb for a medical device includes first and second bodies. The first body has a substantially hemispherical distal side. The second body extends from the first body and includes a mechanical connection point at or near the proximal side of the second body. An instrument channel extends through the optical bulb from the proximal side of the second body to the distal side of the first body. An imaging channel extends an aperture defined in the proximal side of the second body and terminates between the proximal and substantially hemispherical distal sides of the first body. The distal end of the imaging channel is substantially hemispherical. The first body is configured and arranged to provide a substantially uniform image path within a field of view of a camera disposed in the imaging channel.

14 Claims, 24 Drawing Sheets

(56) References Cited

U.S. PATENT DOCUMENTS

| | | | |
|---|---|---|---|
| 4,233,982 A | 11/1980 | Bauer et al. | |
| 4,436,087 A | 3/1984 | Ouchi | |
| 4,535,773 A | 8/1985 | Yoon | |
| 5,025,778 A | 6/1991 | Silverstein et al. | |
| 5,217,001 A | 6/1993 | Nakao et al. | |
| 5,261,391 A | 11/1993 | Inoue | |
| 5,441,503 A | 8/1995 | Considine et al. | |
| 5,454,807 A | 10/1995 | Lennox et al. | |
| 5,632,782 A | 5/1997 | Carlough | |
| 5,660,175 A | 8/1997 | Dayal | |
| 5,797,960 A | 8/1998 | Stevens et al. | |
| 5,842,971 A | 12/1998 | Yoon | |
| 5,855,569 A | 1/1999 | Komi | |
| 5,899,915 A | 5/1999 | Saadat | |
| 5,928,218 A | 7/1999 | Gelbfish | |
| 5,941,815 A | 8/1999 | Chang | |
| 6,033,426 A | 3/2000 | Kaji | |
| 6,129,713 A | 10/2000 | Mangosong et al. | |
| 6,178,346 B1 | 1/2001 | Amundson et al. | |
| 6,293,282 B1 | 9/2001 | Lemelson | |
| 6,309,345 B1 | 10/2001 | Stelzer et al. | |
| 6,315,714 B1 | 11/2001 | Akiba | |
| 6,503,192 B1 | 1/2003 | Ouchi | |
| 6,554,793 B1 | 4/2003 | Pauker et al. | |
| 6,641,562 B1 | 11/2003 | Peterson | |
| 6,689,085 B1 | 2/2004 | Rubenstein et al. | |
| 6,748,559 B1 | 6/2004 | Pfister et al. | |
| 6,749,559 B1 | 6/2004 | Kraas et al. | |
| 7,442,167 B2 | 10/2008 | Dunki-Jacobs et al. | |
| 7,537,562 B2 | 5/2009 | Takano | |
| 7,914,444 B2 | 3/2011 | Moriyama et al. | |
| 8,287,447 B2 | 10/2012 | Gasche et al. | |
| 8,394,015 B2 | 3/2013 | Dibiasio et al. | |
| 8,425,407 B2 | 4/2013 | Sato et al. | |
| 8,491,631 B2 | 7/2013 | Del Nido et al. | |
| 8,926,502 B2 | 1/2015 | Levy et al. | |
| 8,951,275 B2 | 2/2015 | Cannon et al. | |
| 9,451,875 B2 | 9/2016 | Sigmon, Jr. et al. | |
| 9,459,442 B2 | 10/2016 | Miller | |
| 9,709,795 B2 | 7/2017 | Miller | |
| 9,844,394 B2 | 12/2017 | DiBiasio et al. | |
| 2002/0026094 A1 | 2/2002 | Roth | |
| 2002/0068853 A1 | 6/2002 | Adler | |
| 2002/0111585 A1 | 8/2002 | LaFontaine | |
| 2004/0024414 A1 | 2/2004 | Downing | |
| 2004/0111019 A1 | 6/2004 | Long | |
| 2004/0116897 A1 | 6/2004 | Aboul-Hosn | |
| 2004/0193191 A1 | 9/2004 | Starksen et al. | |
| 2005/0197530 A1 | 9/2005 | Wallace et al. | |
| 2005/0234296 A1 | 10/2005 | Saadat et al. | |
| 2005/0234298 A1 | 10/2005 | Kucklick et al. | |
| 2006/0264708 A1 | 11/2006 | Horne | |
| 2007/0066869 A1 | 3/2007 | Hoffman | |
| 2007/0197896 A1 | 8/2007 | Moll et al. | |
| 2008/0208006 A1 | 8/2008 | Farr | |
| 2009/0048486 A1 | 2/2009 | Surti | |
| 2009/0275893 A1 | 11/2009 | DiBiasio et al. | |
| 2010/0286475 A1 | 11/2010 | Robertson | |
| 2011/0288372 A1 | 11/2011 | Petersen | |
| 2011/0295072 A1 | 12/2011 | Boulais et al. | |
| 2012/0116158 A1 | 5/2012 | Hale et al. | |
| 2012/0209074 A1 | 8/2012 | Titus | |
| 2012/0232342 A1 | 9/2012 | Reydel | |
| 2013/0245371 A1* | 9/2013 | Mourlas | A61B 1/018 600/104 |
| 2013/0281779 A1* | 10/2013 | Robertson | A61B 1/00096 600/109 |
| 2014/0213847 A1 | 7/2014 | Green et al. | |
| 2014/0213848 A1 | 7/2014 | Moskowitz et al. | |
| 2014/0221749 A1 | 8/2014 | Grant | |
| 2015/0065795 A1* | 3/2015 | Titus | A61B 1/053 600/104 |
| 2015/0313633 A1 | 11/2015 | Gross et al. | |
| 2016/0000463 A1 | 1/2016 | DiBiasio et al. | |
| 2016/0367120 A1 | 12/2016 | Dupont et al. | |
| 2017/0231477 A1* | 8/2017 | del Nido | A61B 17/3423 600/104 |

FOREIGN PATENT DOCUMENTS

| | | |
|---|---|---|
| WO | 1998024501 A1 | 6/1998 |
| WO | 1998040016 A2 | 9/1998 |
| WO | 20040112652 A2 | 12/2004 |
| WO | 2005051175 A2 | 6/2005 |
| WO | 2007081800 A2 | 7/2007 |
| WO | 2011047339 A2 | 4/2011 |
| WO | 2016205694 A1 | 12/2016 |
| WO | 2017139629 A1 | 8/2017 |

OTHER PUBLICATIONS

International Search Report & Written Opinion, PCT/US07/00270, dated Oct. 1, 2007.

Ataollahi et al., "Cardioscopic Tool-Delivery Instrument for Beating-Heart Surgery," IEEE ASME Transactions on Mechatronics, 21(1):1-1 (abstract), Jan. 2015 [retrieved on Apr. 15, 2019]. Retrieved from the internet: <URL:https://www.researchgate.net/publication/283309805_Cardioscopic_Tool-Delivery_Instrumentfor_Beating-Heart_Surgery>.

International Search Report and Written Opinion in International Application No. PCT/US2016/038147, dated Sep. 8, 2016.

Vasilyev et al.; "A Novel Cardioport for Beating-Heart Image-Guided Intracardiac Surgery"; Children's Hospital Boston, Harvard Medical School, Boston, Massachusetts; Massachusetts Institute of Technology, Cambridge, Massachusetts; International Society for Minimally Invasive Cardiothoracic Surgery (ISMICS); Jun. 3, 2009.

Vasilyev et al.; "Three-Dimensional Echo and Videocardioscopy-Guided Atrial Septal Defect Closure"; Annals of Thoracic Surgery; 2006; vol. 82; pp. 1322-1326.

Vasilyev et al.; "A novel cardioport for beating-heart, image-guided intracardiac surgery" The Journal of thoracic and Cardiovascular Surgery; vol. 142, No. 6; Dec. 2011; pp. 1545-1551.

Padala et al.; Transapical beating heart cardioscopy technique for off-pump visualization of heart valves; The Journal of thoracic and Cardiovascular Surgery; vol. 144, No. 1; 2012; pp. 231-234.

Shiose et al.; "Cardioscopy-guided surgery: Intracardiac mitral and tricuspid valve repair under direct visualization in the beating heart"; The Journal of thoracic and Cardiovascular Surgery; vol. 142, No. 1; 2011; pp. 199-202.

Uchida; "Recent Advances in Percutaneous Cardioscopy"; Curr Cardiovasc Imaging Rep; May 12, 2011; pp. 317-327.

Ahmed et al.; Initial clinical experience with a novel visualization and virtual electrode radiofrequency ablation catheter to treat atrial flutter; Heart Rhythm Society; 2011; pp. 361-367.

International Search Report and Written Opinion in International Application No. PCT/US17/17445, dated Jun. 6, 2017.

Ataollahi et al., "Cardioscopic Tool-Delivery Instrument for Beating-Heart Surgery," IEEE ASME Transactions on Mechatronics, vol. 21, No. 1, Feb. 2016, pp. 584-590.

European Patent Office, "Extended European Search Report", App. No. 17750861.1, dated Sep. 30, 2019, European Patent Office.

Extended European Search Report issued in EP07716358.2 dated Apr. 24, 2014.

P. Dupont; "Invention Disclosure—Cardioscopes"; May 21, 2015; 5pp.

International Search Report & Written Opinion, PCT/US17/17445, dated May 5, 2017, 16 pages.

Extended European Search Report in European Application No. 16812547.4, dated Feb. 21, 2019, 8 pages.

PCT International Preliminary Report on Patentability in International Appln. No. PCT/US2018/021680, dated Sep. 15, 2020, 7 pages.

* cited by examiner

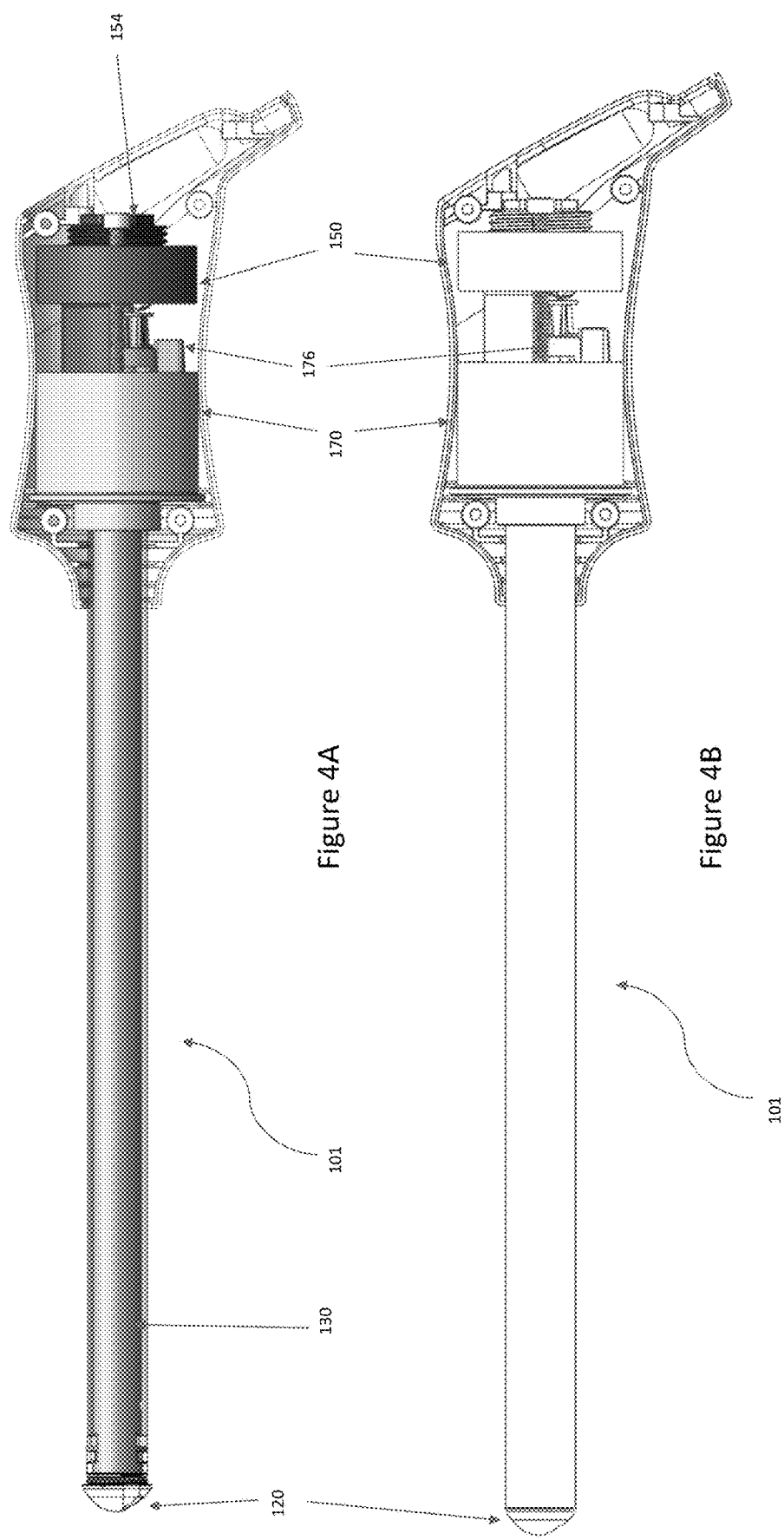

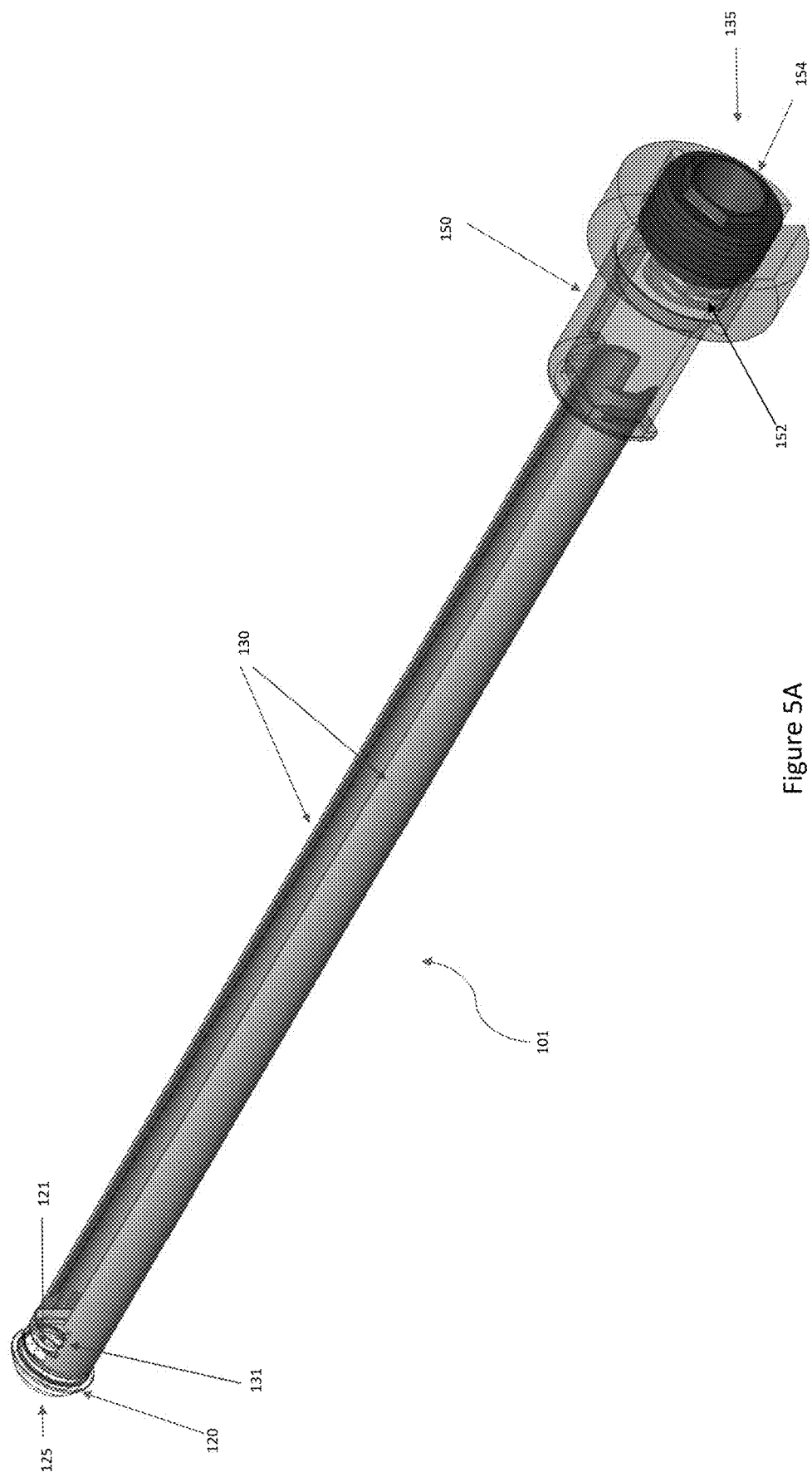

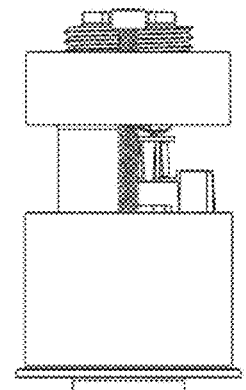
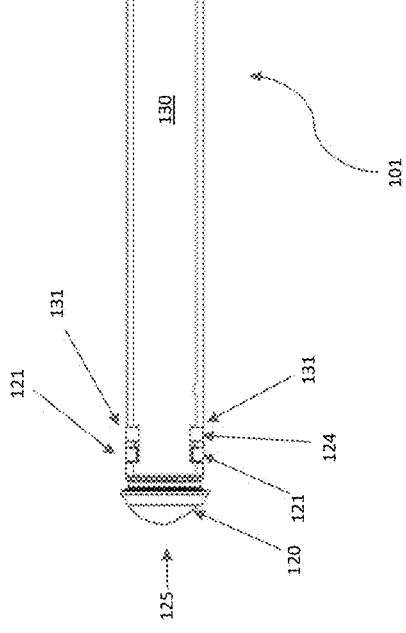
Figure 6A
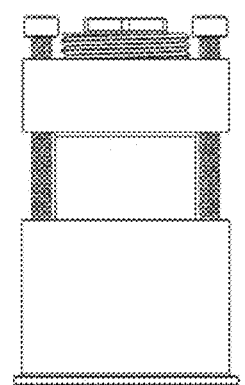
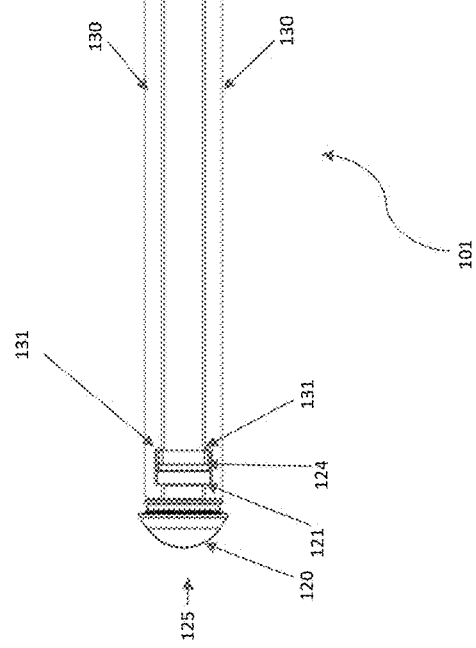
Figure 6B

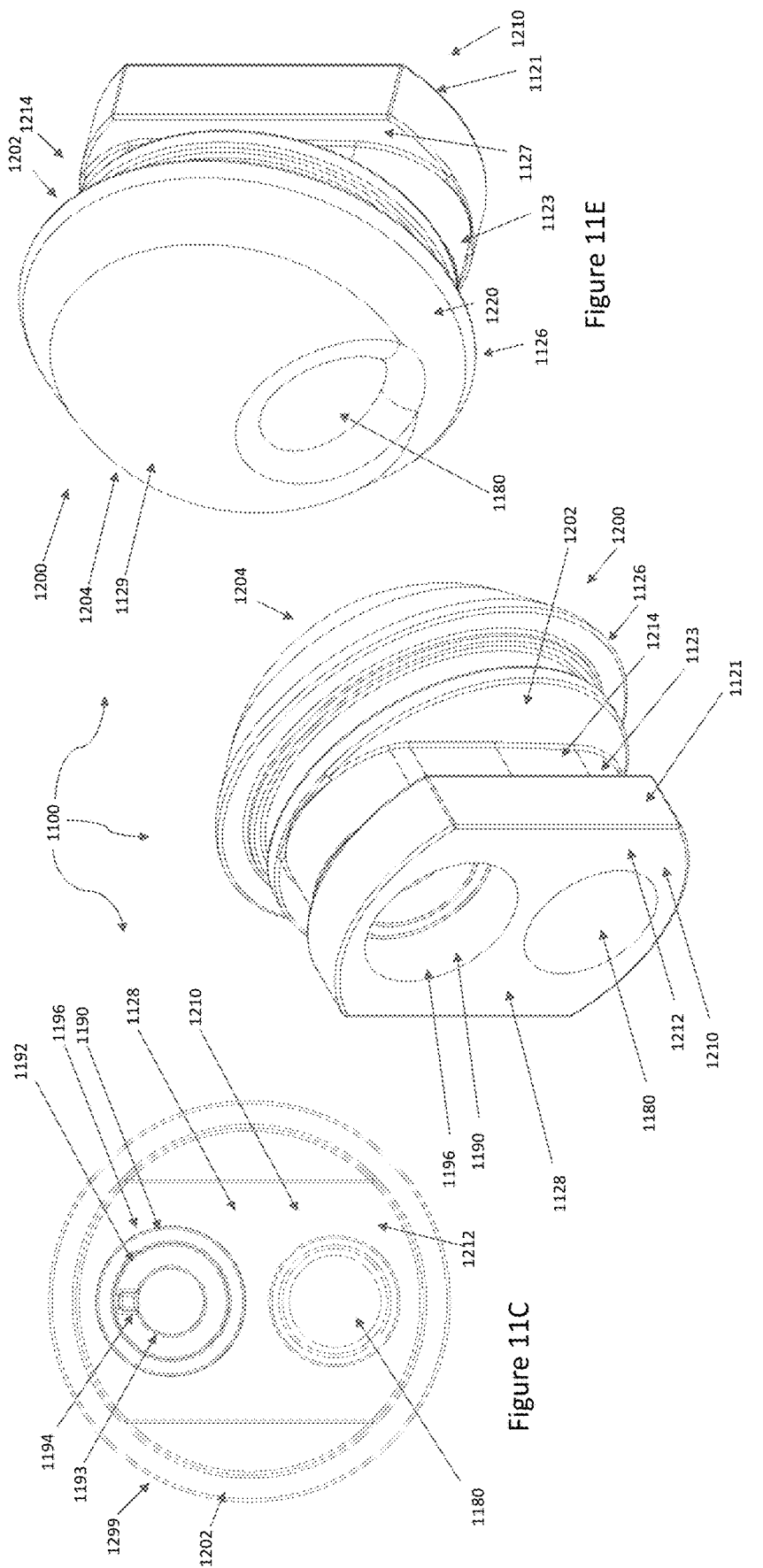

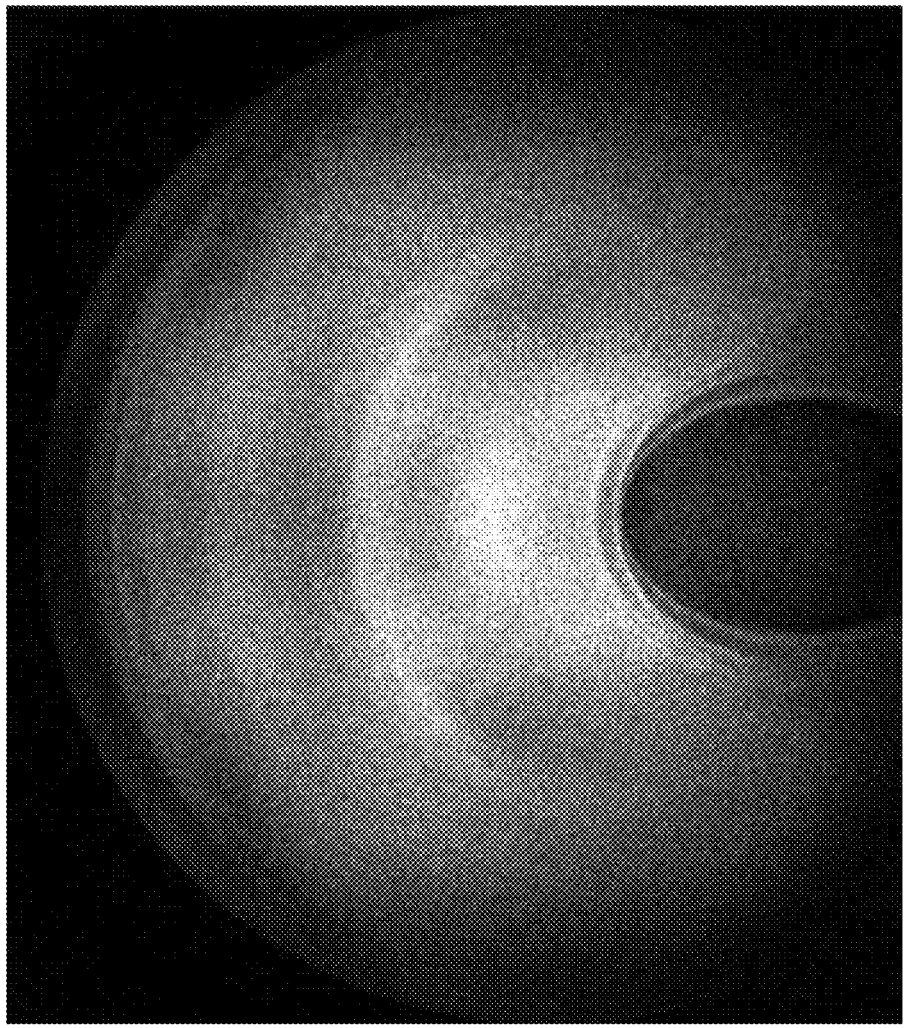
Figure 16

OPTICAL BULB FOR SURGICAL INSTRUMENT PORT

STATEMENT REGARDING FEDERALLY-SPONSORED RESEARCH

This invention was made with U.S. government support under Grant No. 5R42HL132655, awarded by the Heart, Lung, and Blood Institute (NHLBI) of the National Institutes of Health (NIH). The U.S. government has certain rights in the invention.

TECHNICAL FIELD

This application relates generally to devices for minimally invasive image-guided surgery, such as cardiac surgery.

BACKGROUND

Instrument guides or ports can be used to guide the insertion of surgical instruments into a surgical site. Examples of procedures where such instruments ports or guides are used are beating-heart, minimally-invasive cardiac procedures to repair heart defects or to treat vascular heart disease. To position an instrument port at an appropriate location near the surgical site, current systems rely on either the operator's vision or a secondary optical system, such as an endoscope, that is inserted next to or into the instrument guide.

Positioning an instrument using the operator's vision is limited to procedures where the surgical site is within the operator's line-of-sight, and thus cannot be done for most internal surgical sites. One problem with secondary optical systems is that they require a separate imaging channel in the instrument guide to receive the optical system (e.g., an endoscope). This causes the instrument guide to be larger in diameter and more expensive in order to accommodate the separate imaging channel. When the secondary optical system is located next to the instrument guide, it is exposed to the body fluids (e.g., blood) near the surgical site, which limits the clarity, field of view, and/or depth of view of the secondary optical systems. When the secondary optical system contacts body fluids, it increases the risk of infection. This risk is compounded each time that the secondary optical system is introduced to the surgical site.

Current surgical imaging solutions are unable to function effectively in an environment containing body fluids or other biological or surgical debris, contaminants or obstructions. Such fluids and contaminants are generally not optically transparent and have other mechanical and optical characteristics that degrade the functioning of imaging systems during surgery, e.g., in the presence of blood at the aperture of the imaging system, lens or other optical components. This makes the imaging system useless or ineffective in such environments.

Current surgical imaging solutions also suffer from image distortion and/or other issues.

It would be desirable to overcome one or more of these deficiencies.

SUMMARY

The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Other objects, advantages and novel features of the disclosure will be set forth in the following detailed description of the disclosure when considered in conjunction with the drawings.

An aspect of the invention is directed to an optical bulb for a medical device, the bulb comprising: a first body having a substantially hemispherical distal side; a second body extending from a proximal side of the first body, the second body including a mechanical connection point disposed at or near a proximal side of the second body; an instrument channel extending from the proximal side of the second body to the substantially hemispherical distal side of the first body; an imaging channel that extends from an aperture defined in the proximal side of the second body, the imaging channel terminating between the proximal and substantially hemispherical distal sides of the first body, wherein a distal end of the imaging channel is substantially hemispherical, wherein the first body is configured and arranged to provide a substantially uniform image path within a field of view of a camera disposed in the imaging channel.

In one or more embodiments, the substantially hemispherical distal end of the imaging channel has a negative power to increase the field of view of the camera. In one or more embodiments, the substantially hemispherical distal end of the imaging channel is configured to refract light passing out of the imaging channel towards the instrument channel. In one or more embodiments, the substantially hemispherical distal end of the imaging channel eliminates a total internal reflection of light at a wall of the instrument channel.

In one or more embodiments, a light source for the camera is located outside of the imaging channel. In one or more embodiments, the light source is disposed in a counterbore of the imaging channel. In one or more embodiments, the light source is integrated with the camera. In one or more embodiments, the location of the light source and an inner cross-sectional diameter of the imaging channel are selected to reduce a reflection of light within the imaging channel, the light emitted by the light source. In one or more embodiments, the inner cross-sectional diameter is about 2.5 mm. In one or more embodiments, the light emitted by the light source is substantially uniform distally from the first body within the field of view of the camera. In one or more embodiments, the light source comprises a plurality of light elements, each light element disposed along a virtual circle, wherein the camera is disposed in a center of the virtual circle. In one or more embodiments, the light elements comprise light emitting diodes.

In one or more embodiments, the first and second bodies comprise a same material. In one or more embodiments, the same material comprises an acrylic thermoplastic. In one or more embodiments, the mechanical connection point comprises a flange.

Another aspect of the invention is directed to an apparatus comprising: a housing having a surface for a user to hold the apparatus; a shaft that extends from the housing, the shaft including a port body having first and second channels; an optical bulb disposed at a distal end of the shaft, the optical bulb comprising: a first body having a substantially hemispherical distal side; a second body extending from a proximal side of the first body, the second body including a mechanical connection point disposed at or near a proximal side of the second body; an instrument channel extending from the proximal side of the second body to the substantially hemispherical distal side of the first body, the instrument channel aligned with the first channel in the port body;

an imaging channel that extends from an aperture defined in the proximal side of the second body, the imaging channel terminating between the proximal and substantially hemispherical distal sides of the first body, the imaging channel aligned with the second channel in the port body, wherein a distal end of the imaging channel is substantially hemispherical, wherein the first body is configured and arranged to provide a substantially uniform image path within a field of view of a camera disposed in the imaging channel.

In one or more embodiments, the substantially hemispherical distal end of the imaging channel has a negative power to increase the field of view of the camera. In one or more embodiments, the substantially hemispherical distal end of the imaging channel is configured to refract light passing out of the imaging channel towards the instrument channel. In one or more embodiments, the substantially hemispherical distal end of the imaging channel eliminates a total internal reflection of light at a wall of the instrument channel.

In one or more embodiments, a light source for the camera is located outside of the imaging channel. In one or more embodiments, the light source is disposed in a counterbore of the imaging channel. In one or more embodiments, the light source is integrated with the camera. In one or more embodiments, the location of the light source and an inner cross-sectional diameter of the imaging channel are selected to reduce a reflection of light within the imaging channel, the light emitted by the light source. In one or more embodiments, the inner cross-sectional diameter is about 2.5 mm. In one or more embodiments, the light emitted by the light source is substantially uniform distally from the first body within the field of view of the camera. In one or more embodiments, the light source comprises a plurality of light elements, each light element disposed along a virtual circle, wherein the camera is disposed in a center of the virtual circle. In one or more embodiments, the light elements comprise light emitting diodes.

In one or more embodiments, the first and second bodies comprise a same material. In one or more embodiments, the same material comprises an acrylic thermoplastic. In one or more embodiments, the mechanical connection point comprises a flange.

BRIEF DESCRIPTION OF THE DRAWINGS

For a fuller understanding of the nature and advantages of certain aspects of the invention, reference is made to the following detailed description of preferred embodiments and in connection with the accompanying drawings, in which:

FIGS. 4A and 4B are side views.

FIGS. 5A and 5B are simplified perspective and side views, respectively, of the instrument port disclosed herein, with certain components not shown in order to illustrate mechanical aspects of the invention, according to one or more embodiments;

FIGS. 6A and 6B are simplified side and top views, respectively, of the instrument port disclosed herein, according to one or more embodiments;

FIGS. 11A, 11B, 11C, 11D and 11E are side, front (distal), rear (proximal), rear perspective and front perspective views, respectively, of a bulb comprising a distal portion of the instrument port disclosed herein, according to one or more embodiments;

FIG. 16 is a simulated illumination distribution outside the distal end of the bulb of FIG. 15;

DETAILED DESCRIPTION

An optical bulb for a medical device provides a substantially uniform image path within a field of view of a camera disposed in an imaging channel in the bulb. The imaging channel can have a substantially hemispherical distal end. The bulb also includes first and second bodies, the second body extending from the first body. The first body has a substantially hemispherical distal side. The proximal side of the second body has a mechanical connection point that can be pulled mechanically towards the proximal side of the apparatus to secure the optical bulb to the apparatus and to create a fluid-tight seal by pulling the proximal side of the optical bulb against a gasket.

Figure 1A:
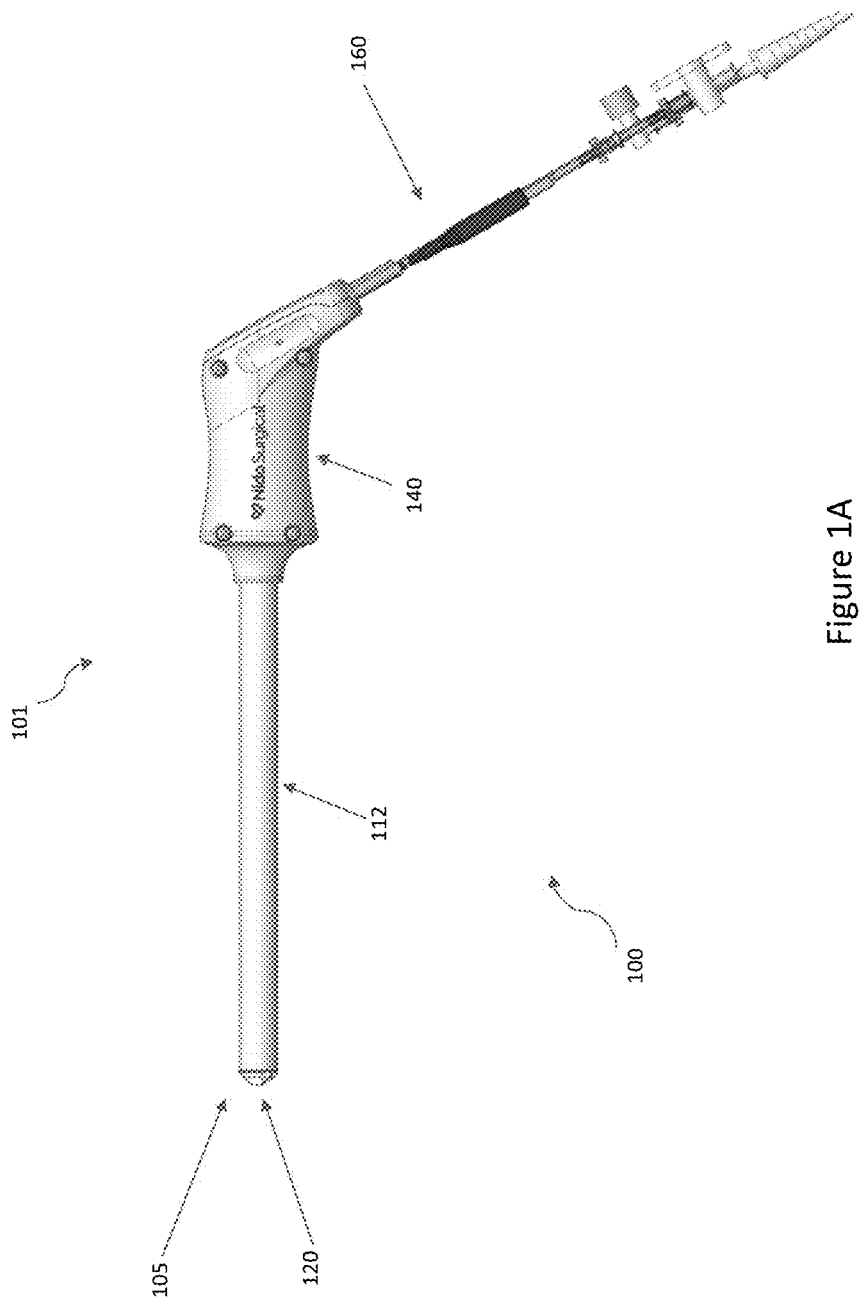
FIGS. 1A and 1B are side views.
Figure 1B:
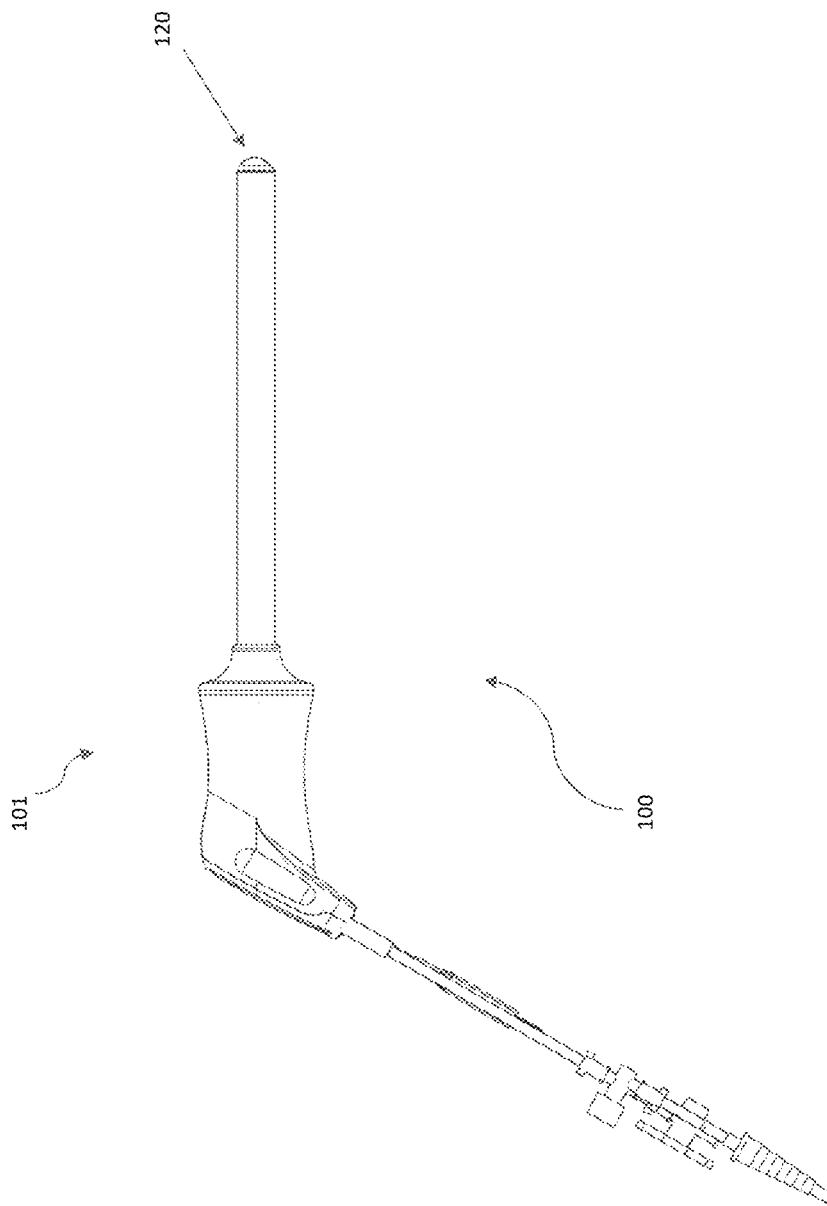
Figure 1C:
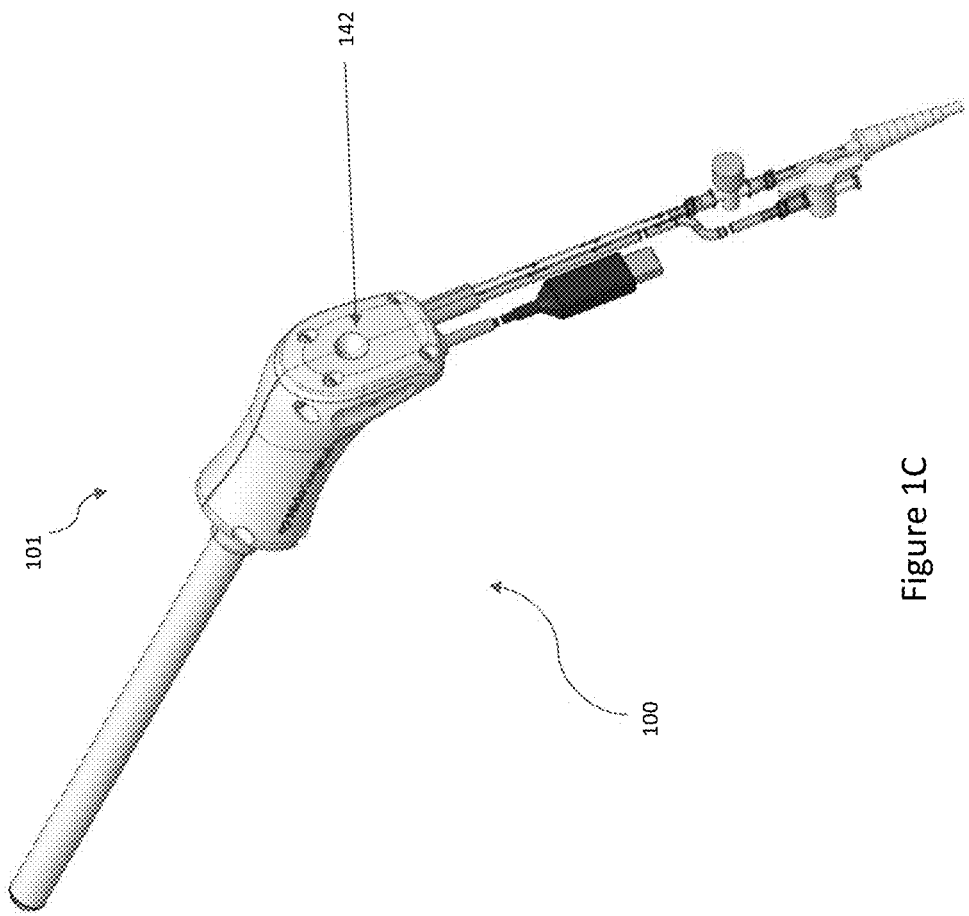
FIG. 1C is a perspective view, of a surgical apparatus including the instrument port disclosed herein, according to one or more embodiments.

FIGS. 1A, 1B and 1C show an exemplary surgical apparatus 100 comprising an instrument port 101 with a distal tip 105, with FIGS. 1A and 1B being side planar views and FIG. 1C being a perspective view. The instrument port 101 comprises bulb 120 at its distal tip 105, a shaft that includes a port body (not illustrated) contained within sleeve 112, and other components contained within housing 140, which may be used by the surgeon as a handle to manipulate and guide the apparatus 100 (e.g., by handling a surface of housing 140). The proximal face of housing 140 has an opening 142 for an instrument channel that extends to the distal tip 105 of the instrument port 101 for introducing or guiding the surgical instrument port into a surgical site inside the patient's body while being manipulated from outside the patient's body. The underside of housing 140 has connections to fluid and electrical lines 160, the latter for use in powering and/or receiving data from an imaging system that can be disposed in the distal tip 105.

Figure 2:
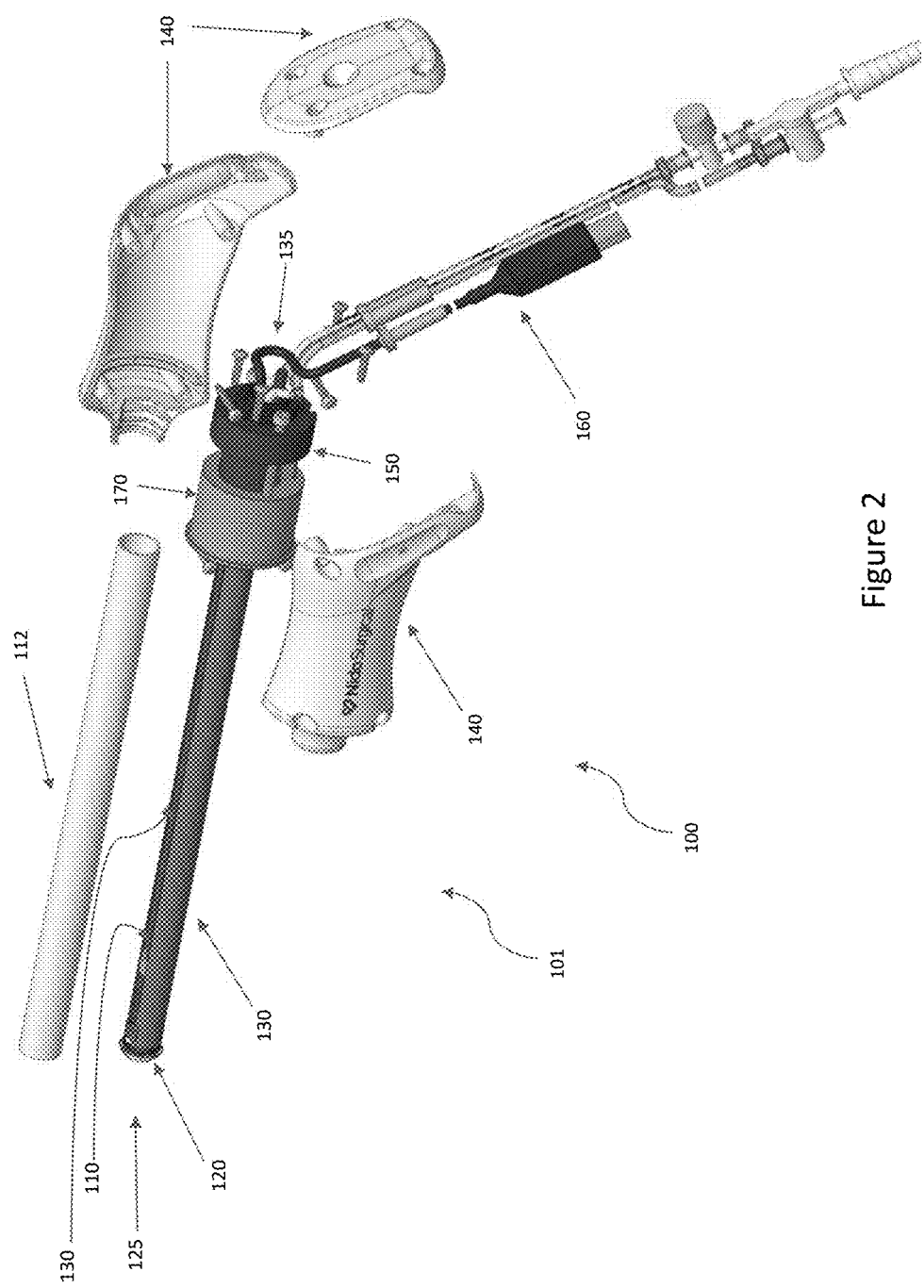
FIG. 2 is an exploded perspective view of the apparatus of FIGS. 1A and 1B, according to one or more embodiments.

FIG. 2 illustrates a partly exploded perspective view of instrument port 101. In this view, sleeve 112 and housing 140 are separated from the remainder of the apparatus 100, allowing interior parts to be seen. Inside of sleeve 112 is port body 110, with connecting rods 130 alongside it on each side. The connecting rods 130 connect to a proximal side of the bulb 120 to secure and pull the proximal side of the bulb 120 to/against a gasket to provide a fluid seal therebetween. The port body 110 is seated within base body 150 at proximal end 135, and the base body and port body are partly enclosed by collar 170. Electrical and fluidic connections 160 can be seen extending beyond base body 150 in the proximal direction.

Figure 3:
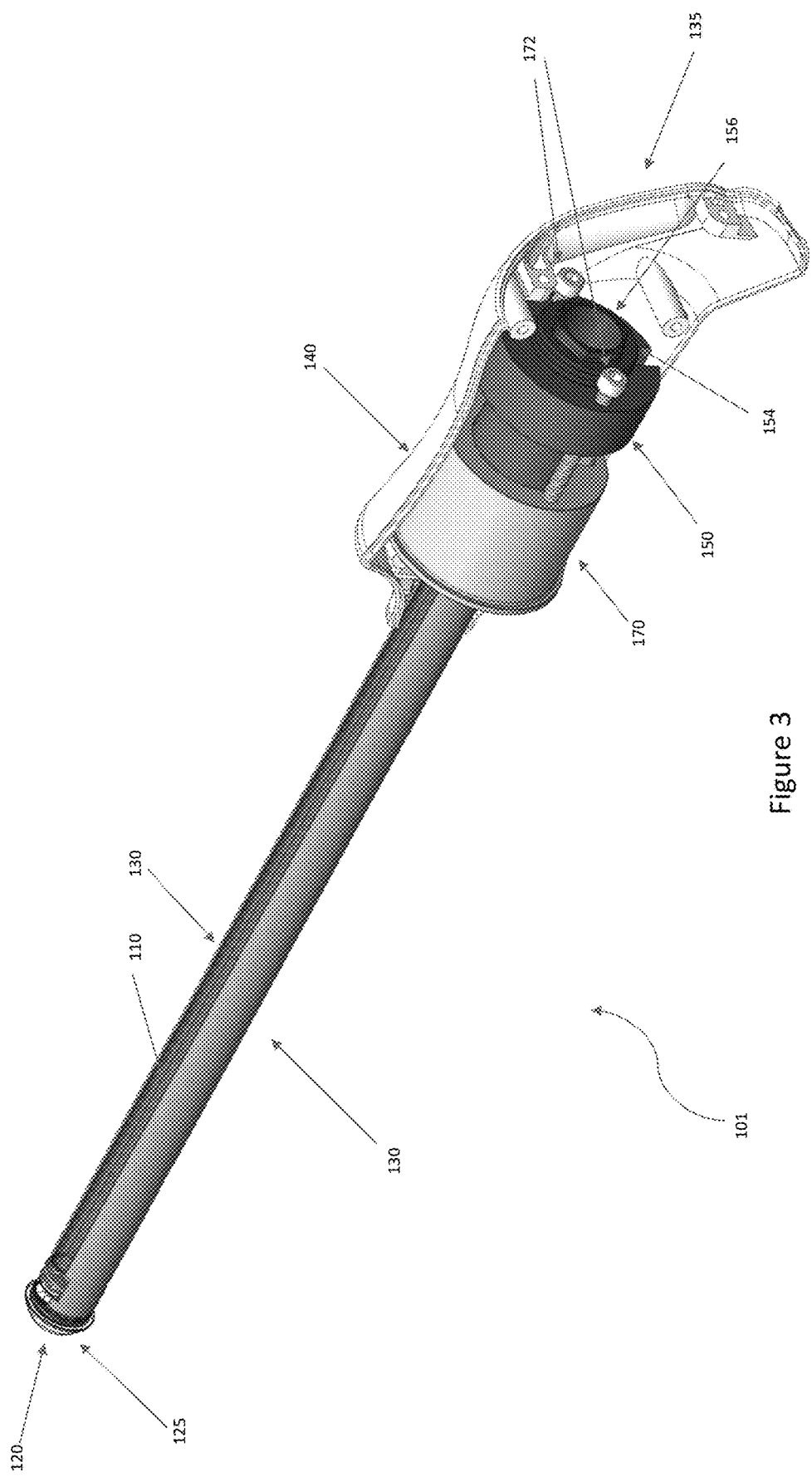
FIG. 3 is a cutaway perspective view of a portion of a surgical apparatus including the instrument port disclosed herein, according to one or more embodiments.

FIG. 3 shows in perspective view the internal parts of instrument port 101 in more detail, focusing on the mechanical aspects of the assembly. Sleeve 112, part of housing 140 and connecting electrical and fluidic lines 160 from FIGS. 1-2 are not shown. Base body 150 fits into the proximal end of collar 170 and bolts 172 rest against and apply pressure to the proximal end of collar 170 to lock the forward position of collar 170. End cap 154 is threaded into the proximal end 135 of base body 150. End cap 154 contains a channel 156 through which electrical and fluidic connections are made to the instrument port, and through which a surgical instrument may be inserted.

FIGS. 4A and 4B show a side view of the instrument port 101 as illustrated in FIG. 3. As discussed, a proximal end of distal bulb 120 is pulled against a gasket by connecting rods 130.

Figure 4C:
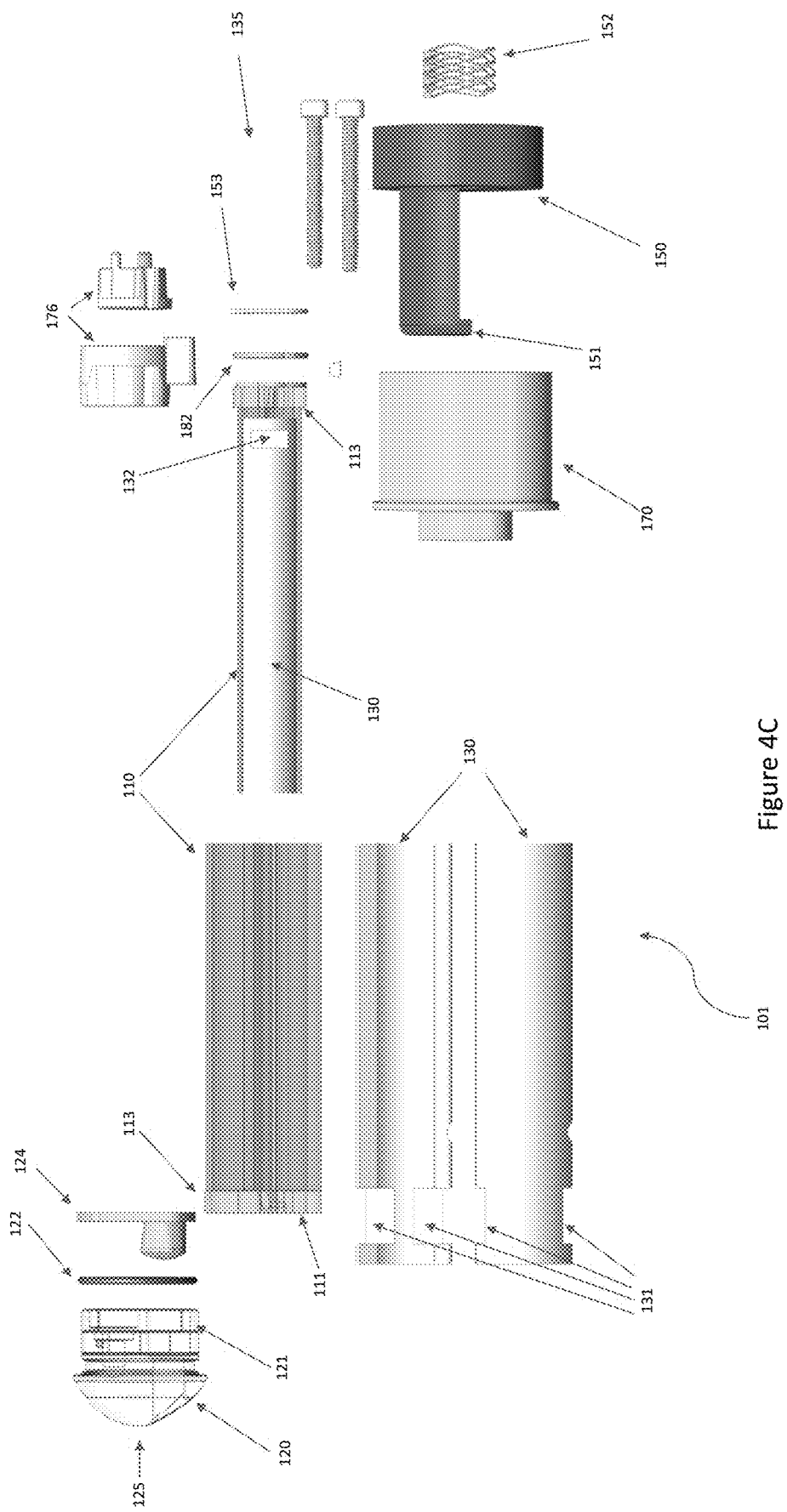
FIG. 4C is an exploded side view, of a portion of a surgical apparatus including the instrument port disclosed herein, according to one more embodiments.

FIG. 4C shows an exploded side view of the instrument port 101 as viewed in FIGS. 4A and 4B. Between bulb 120 and distal end 111 of port body 110 are O-ring seal 122 and valve gasket 124. The O-ring seal 122 seals the bulb 120 to the sleeve 112, and the valve gasket 124 seals the bulb 120 to the port body 110. At proximal end 135 of port body 110, disposed between the proximal end 135 and base body 150, are additional components 176 as well as gasket 182 and washer 153. Washer 153 rests against distal end of spring 152, whose proximal end is adjacent to base cap 154 of FIG. 4A (not shown in FIG. 4C). The port body 110 can optionally include faceplates 113 at its distal end 111 and at its proximal end. The faceplates 113 can be a segment of the port body 110 that includes a different cross-sectional diameter and/or one or more channels that are disposed at an angle (other than 180 degrees) with respect to one or more corresponding channels in the port body 110. The faceplates 113 can be manufactured separately to reduce manufacturing costs and complexity. In other embodiments, the port body 110 can be manufactured to include the faceplate 113 segments as a single integral unit.

In operation, the base cap 154 is threaded into the base body 150 to compress the spring 152. The compressed spring 152 pushes in the distal direction on washer 153, additional component 176A, gasket 182, and port body 110. In turn, the port body 110 pushes on the valve gasket 124 and bulb 120, which is mechanically connected to connecting rods 130 to provide the compression needed to form a fluid seal, as discussed below.

The connecting rods 130 are used to mechanically affix the various components of the instrument port to each other, and to maintain sufficient compression against seals and gaskets so as to maintain fluidic integrity of the system, even while the apparatus is subject to mechanical stresses during use. The connecting rods, which function as mechanical tension members, may be made of aluminum (e.g., cast and/or extruded aluminum) in some embodiments. As shown in FIG. 4C, connecting rods 130 comprise notches 131 at distal end 125; these notches 131 mechanically engage with flanged portion 121 of bulb 120. At proximal end 135, connecting rods 130 comprise notches 132 that mechanically engage with flanged portion 151 of base body 150. In some embodiments, flanged portion 121 can include or can be another mechanical connection point, as discussed below. In one or more examples, the connecting rods may comprise the notches said bulb includes a flange. But those skilled in the art will appreciate that the design could may have a different connection feature if the bulb has a connection feature other than a flange. Similarly, the base body may incorporate appropriate mechanical connecting features so as to best suit the mating and coupling points to the remaining components herein.

Figure 5B:
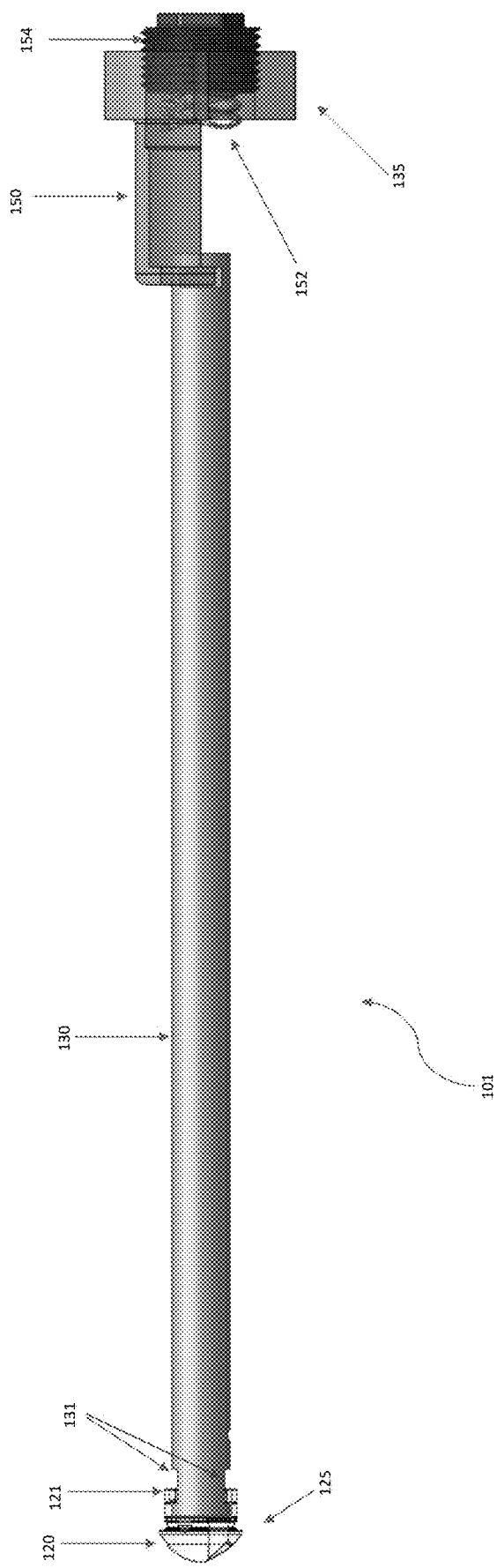

FIGS. 5A and 5B show, in perspective and side views respectively, the mechanical connection between connecting rods 130 and base body 150 and between connecting rods 130 and bulb 120. Other portions of instrument port 101 are not shown in order to better illustrate these mechanical connections. Bulb 120 is at distal end 125 of the apparatus 100, with notches 131 in the distal ends of connecting rods 130 engaged with proximal flanged portion 121 (and/or other mechanical connection point) of bulb 120. At the proximal end 135 of the apparatus, base body 150 is shown, partially transparent for illustrative purposes, along with end cap 154 and spring 152; base body 150 is mechanically engaged with connecting rods 130 at their proximal ends.

FIGS. 6A and 6B show, in side and top views respectively, a bulb 120 attached to and forming a part of an instrument port 101 at distal end 125 thereof, according to some embodiments. As illustrated, notches 131 in connecting rods 130 engage mechanically with flanged portion 121 of bulb 120 to pull the flanged portion 121 (and/or other mechanical connection point) towards valve gasket 124. In FIG. 6A one connecting rod 130 is seen in the foreground, with the other being obscured from view. In FIG. 6B, two connecting rods 130 can be seen, one on either side, viewed from above.

Figure 7:
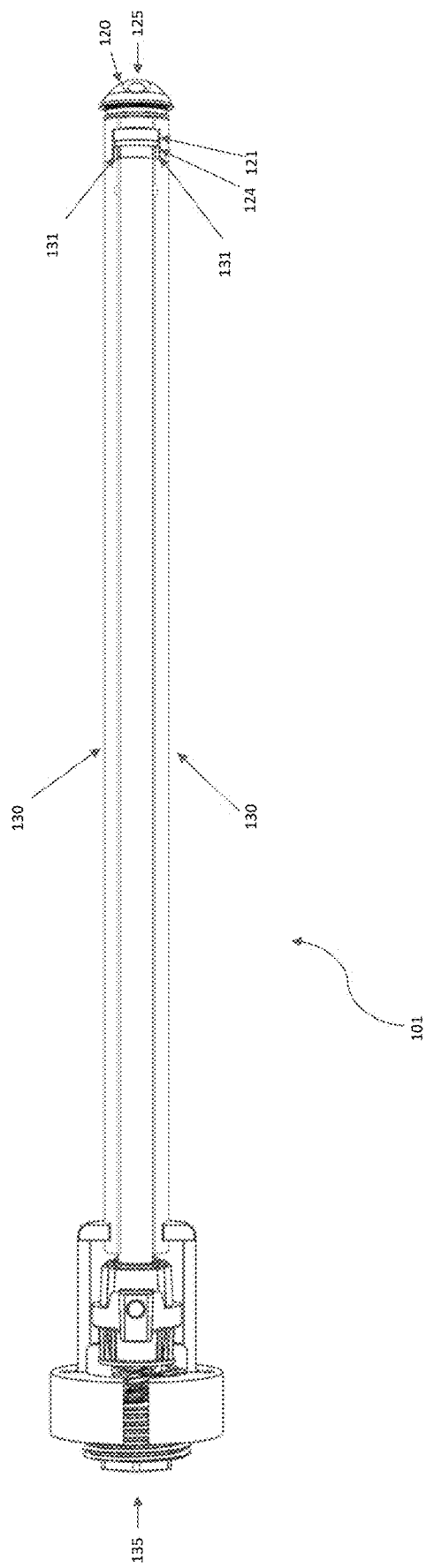
FIG. 7 is a simplified side view of the instrument port disclosed herein, with certain components omitted in order to illustrate internal components, according to one or more embodiments.

FIG. 7 presents a similar view to that of FIG. 6B, in which other parts are visible at proximal end 135 of connecting rods 130.

Figure 8A:
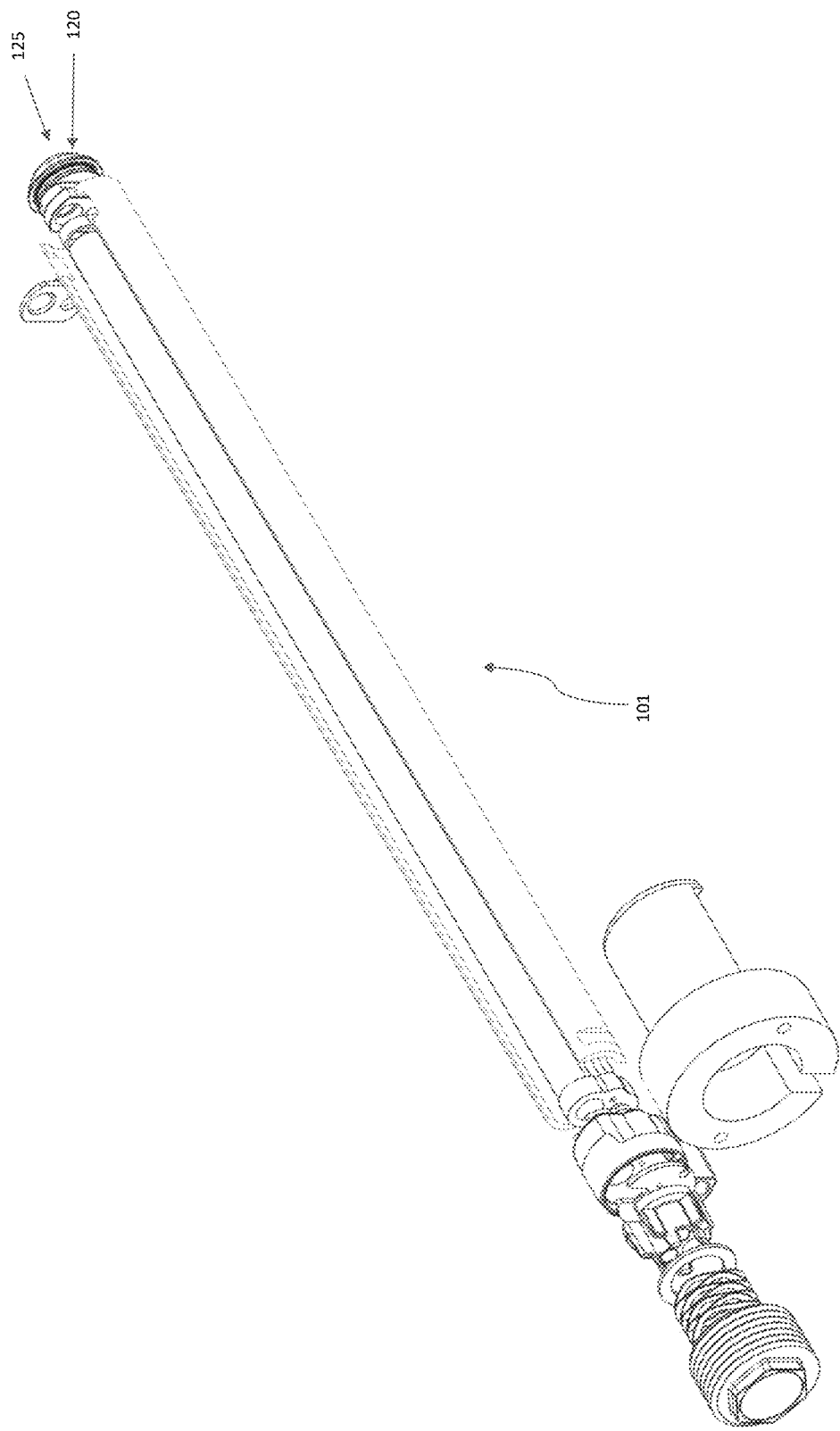
FIG. 8A is an exploded perspective view of the instrument port disclosed herein, according to one or more embodiments.
Figure 8B:
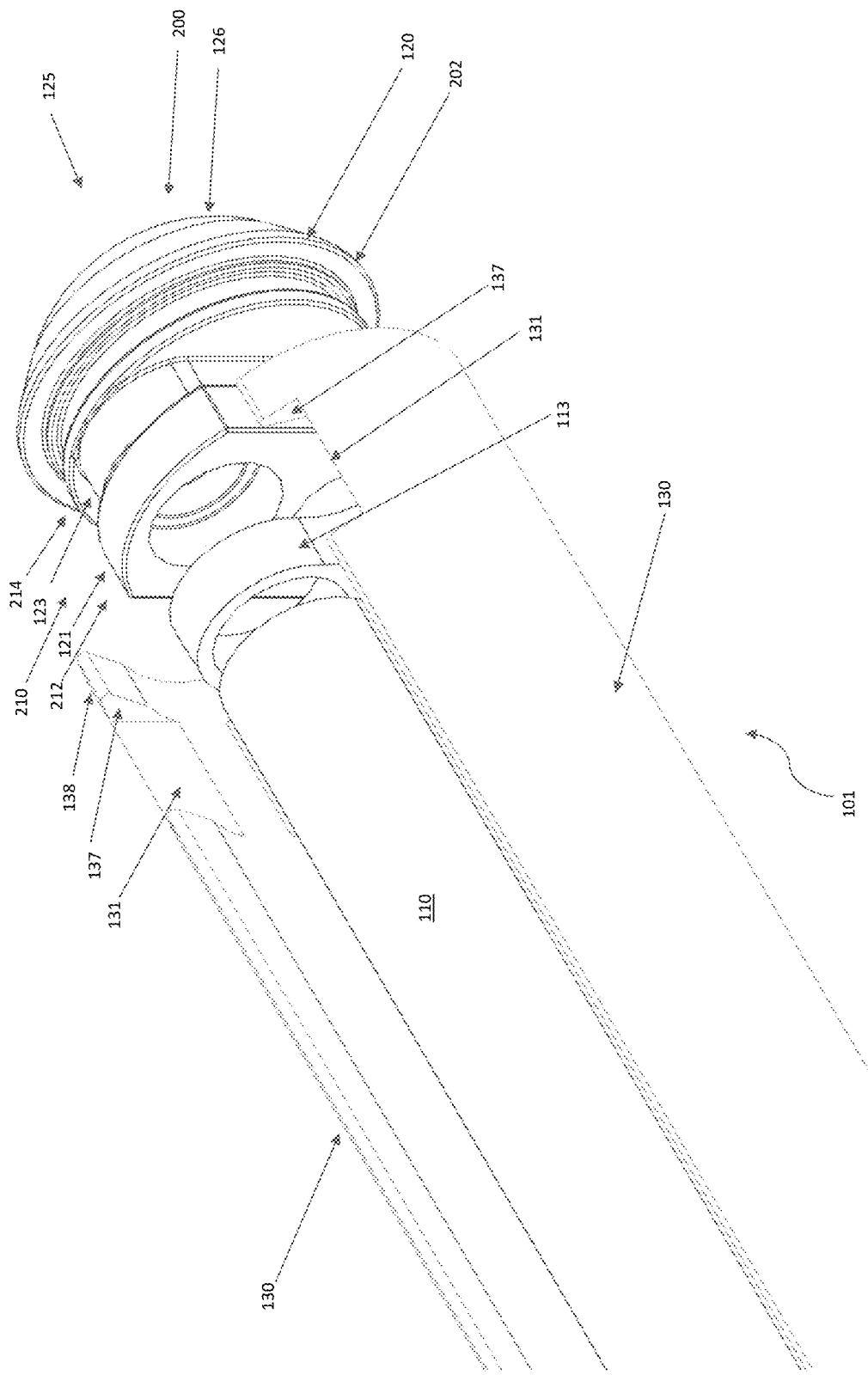
FIG. 8B is an enlarged view of the distal portion of the apparatus illustrated in FIG. 8A.

FIGS. 8A and 8B show exploded perspective views of a portion of instrument port 101 according to one or more embodiments. Distal end 125, including bulb 120, are shown in greater detail in FIG. 8B. Bulb 120 includes flanged portion 121 at its proximal end, narrowed portion 123 distal to flanged portion 121, and rounded or hemispherical portion 126 at its distal end.

As can be seen, bulb 120 includes a first body 200 and a second body 210 extending from a proximal side of the first body. The first body 200 has a hemispherical or substantially hemispherical distal side, which may be referred to as hemispherical portion 126. The proximal side 202 of the first body 200 is planar or substantially planar. The second body 210 includes one or more mechanical connection points, which may be referred to in this disclosure as a flange or flanged portion 121, at or near the proximal side 212 of the second body. The flange defines the narrowed portion 123 in the distal portion 214 of the second body 210. The mechanical connection point(s) can include one or more recesses and/or indentations defined in the second body 210, one or more grooves and/or slots defined in the second body 210, one or more cavities and/or holes defined in the second body 210, one or more ridges or raised edges on the second body 210, or other mechanical connection point.

Proximal to bulb 120 is port body 110, which includes distal faceplate 113. The valve gasket 124 (not illustrated) is disposed between the distal faceplate 113 and the bulb 120. Connecting rods 130 are on either side of port body 110; each connecting rod 130 includes, near its distal end, notch 131 or alternate connection feature, which includes proximal-facing surface 137. Bulb 120 is configured so that flanged portion 121 (and/or other mechanical connection point) mechanically engages with notches 131 (and/or other complementary mechanical connection point, such as a pin or other mechanical extension, a bolt, etc.) such that a portion of proximal-facing surface 137 is in contact with a portion of the distal-facing surface (not shown) of flanged portion 121 of bulb 120, such that the notches 131 can pull the proximal-facing surface 137 towards the valve gasket 124 and port body 110 to form a fluid seal. Connecting rods 130 comprise portion 138 at their distal ends, distal to notches 131; bulb 120 is configured so that portion 138 will fit within the space alongside narrowed portion 123 of bulb 120.

Figure 9A:
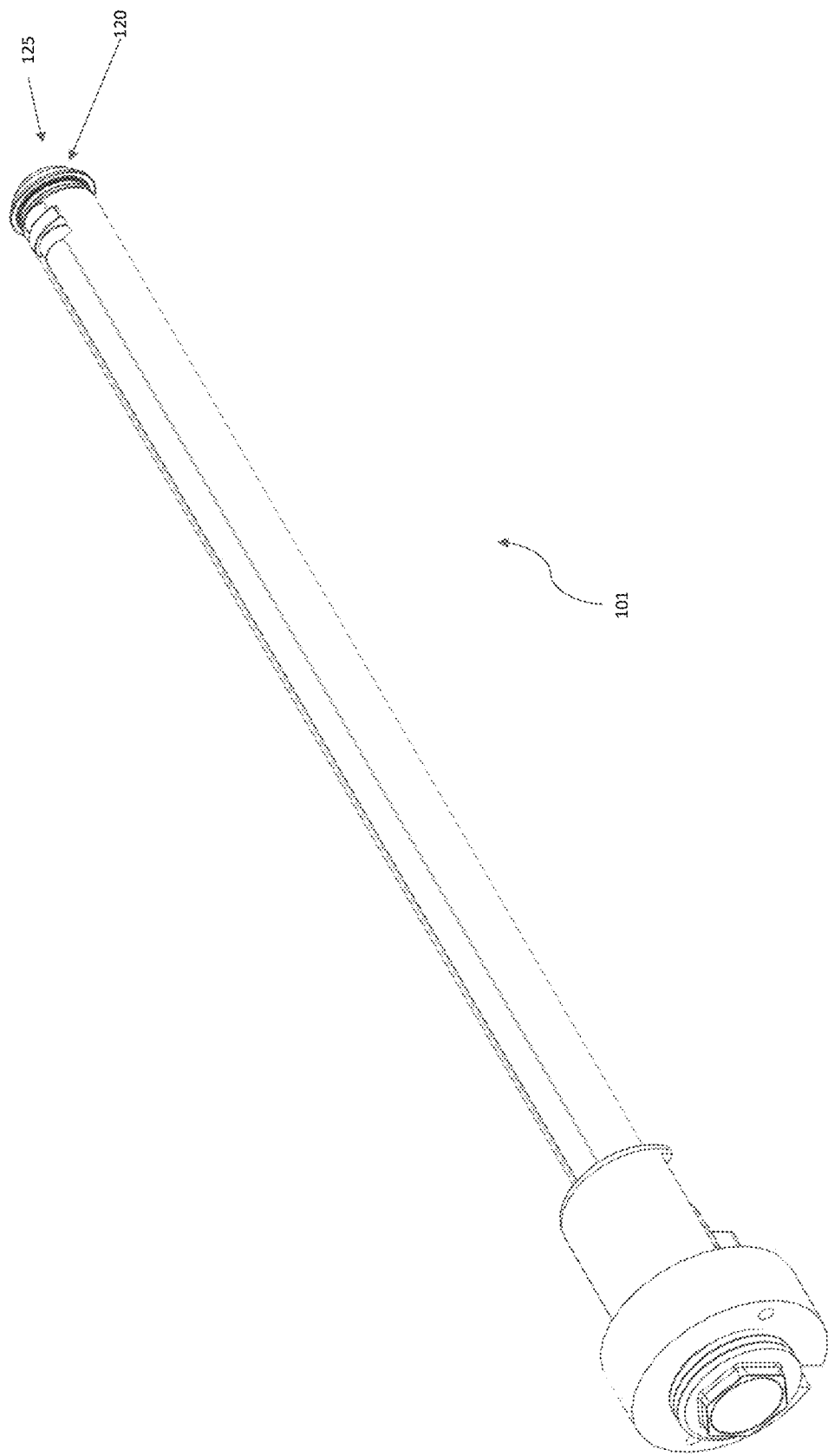
FIGS. 9A and 9B are perspective and bottom views, respectively, of the instrument port disclosed herein, with certain components omitted in order to illustrate mechanical features, according to one or more embodiments.
Figure 9B:
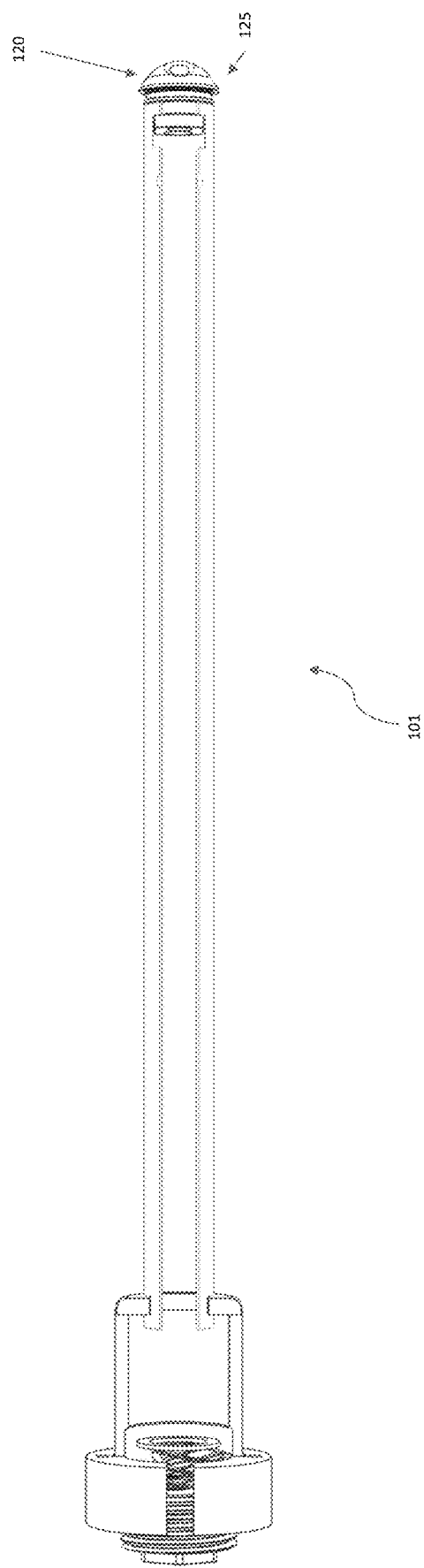
Figure 10:
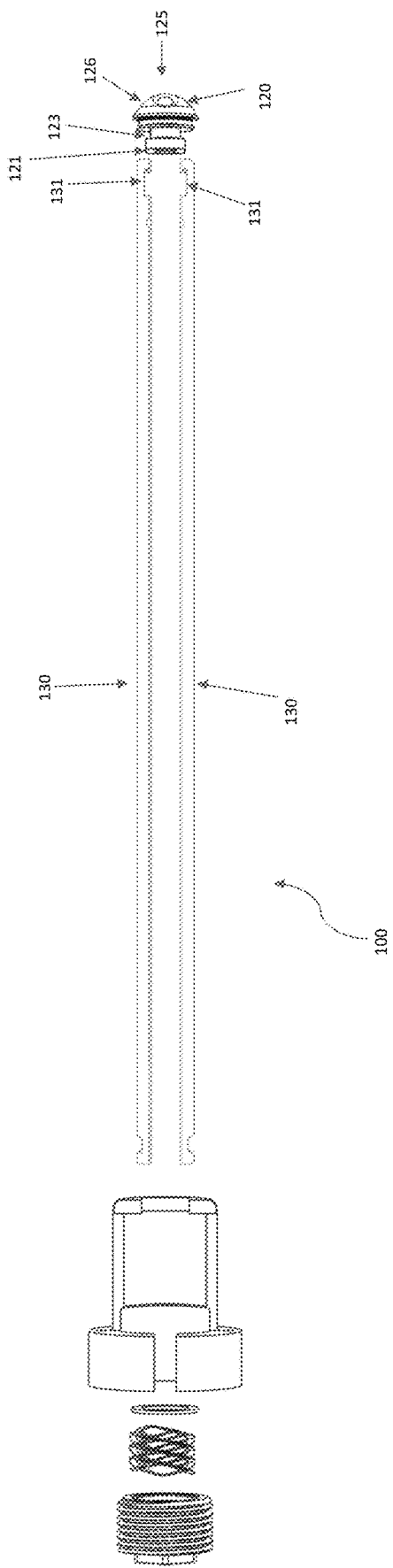
FIG. 10 is an exploded view of the components of the instrument port as depicted in FIG. 9B.

FIGS. 9A and 9B show perspective and side views, respectively, of a portion of instrument port 101 that includes a distal bulb 120 as disclosed herein at distal end 125 thereof, according to one or more embodiments. FIG. 10 shows an exploded side view of the instrument port 101 as seen in FIGS. 9A and 9B. Again, bulb 120 can be seen at distal end 125 of the apparatus, with the bulb including flanged portion 121 (and/or other mechanical connection point) and narrowed portion 123, for engagement with notches 131 (and/or other complementary mechanical connection point) of connecting rods 130.

Figure 11B:
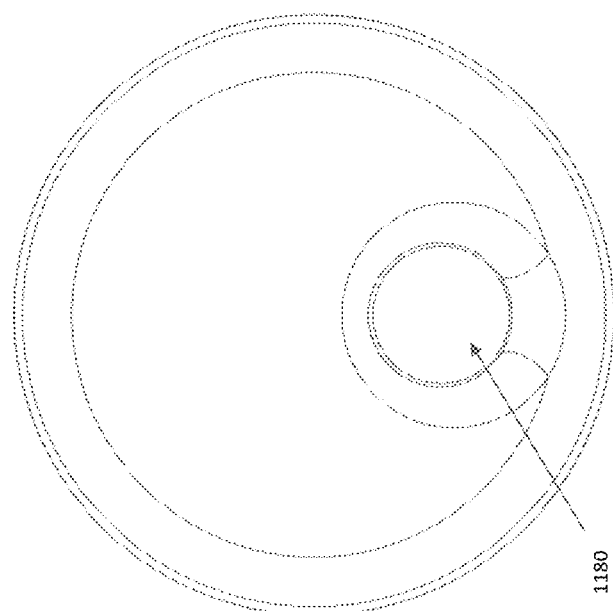
Figure 11A:
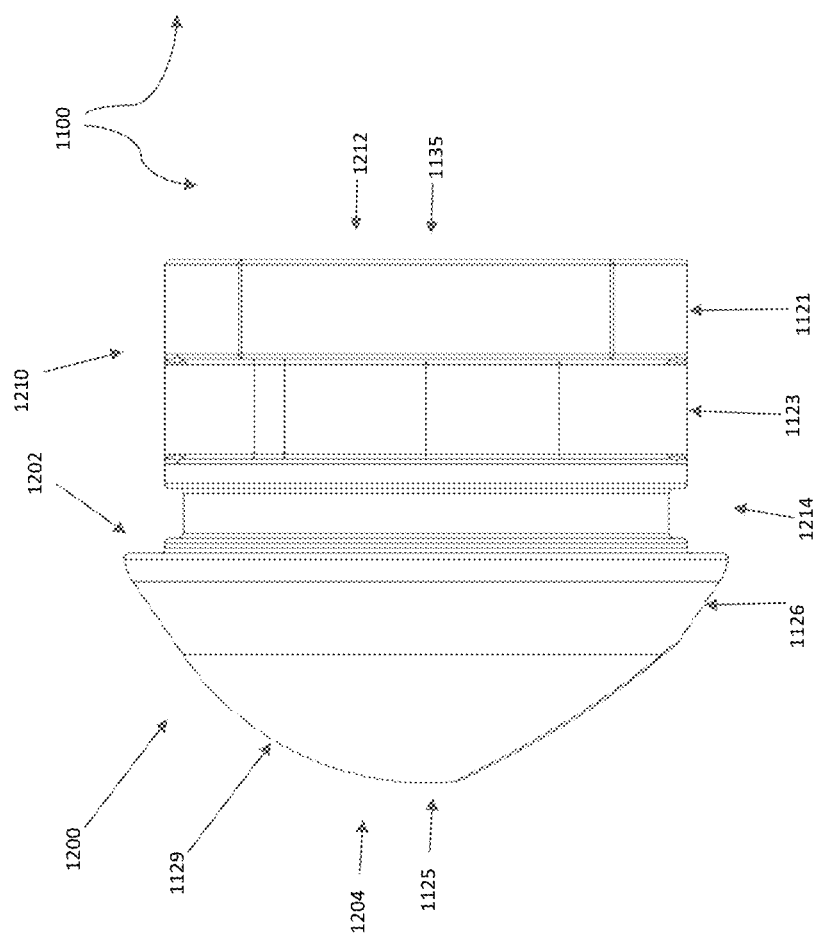

FIGS. 11A-E show various views of a distal tip of a surgical device comprising a bulb, according to one or more embodiments of the invention disclosed herein. Bulb 1100 (which may be the same as or similar to bulb 120 as described herein) is seen in side view in FIG. 11A, in front view (i.e. as viewed from the distal end) in FIG. 11B and in rear view (i.e. as viewed from the proximal end) in FIG. 11C. FIGS. 11D and 11E show perspective views, with the proximal face visible in FIG. 11D and the distal face visible in FIG. 11E.

Bulb 1100 comprises rounded distal portion 1126, narrowed central portion 1123 and flanged proximal portion 1121, all rigidly attached to one another and/or comprising a single piece of material and/or comprising the same material. In some embodiments, the single piece of material and/or the same material is injection molded with an acrylic thermoplastic. An example of an acrylic thermoplastic material is CYROLITE® MD (e.g., CYROLITE® MD H12), available from Evonik Performance Materials GmbH. CYROLITE® MD H12 was formally known as CRYOLITE® MD H12. Distal portion 1126 has a rounded, convex exterior distal surface 1129, whose shape has optical properties as described elsewhere herein. Flanged proximal portion 1121 has a flat proximal exterior surface 1128; other shapes for such proximal exterior surface 1128 may be present in other embodiments. Proximal exterior surface 1128 is configured to mate with a corresponding surface of a valve gasket, which may be the same as or similar to valve gasket 124 of FIG. 4C, or similar component that helps maintain the fluidic isolation and integrity of the different parts of the system of which the bulb 1100 is a part. Flanged proximal portion 1121 can be the same as or substantially the same as flanged portion 121, discussed above.

Bulb 1100 comprises an instrument channel 1180 extending from its proximal surface 1128 to its distal surface 1129, through which a surgical instrument can pass for use inside the body of a patient, such as in a surgical site. Such an instrument would extend from the proximal end of an instrument port or other surgical apparatus of which bulb 1100 is a part, outside of the patient's body, though a first channel contained in a port body that extends into the patient's body during use. In a typical embodiment, the distal end of the port body and the proximal face 1128 of the bulb would have a valve gasket disposed between them, allowing a surgical instrument to be deployed through an instrument channel in the port body, though a valve in the valve gasket, and through the instrument channel 1180 in the bulb, to reach the relevant tissue or space inside the patient's body.

The bulb 1100 comprises an imaging channel 1190, seen in FIGS. 11C-D, open to the proximal face 1128 and closed to the distal face 1129 of the bulb. The imaging channel 1190 extends from an aperture 1196 defined in the proximal side or face 1128 and terminates between the proximal and distal sides or faces 1128, 1129 of the bulb 1100. Imaging channel 1190 is fluidically isolated from instrument channel 1180. Imaging channel 1190 is configured to receive and/or retain an imaging system 1192, which comprises camera 1193 and illumination source 1194. The distal portion 1126 of the bulb 1100 is formed of a material that is at least partly optically transparent to one or more wavelengths of light emitted by illumination source 1194, allowing the camera 1193 to capture images of the surgical site, including the patient's bodily tissue and any surgical instruments being used at the site. The illumination source 1194 may comprise one or more light-emitting diodes (LEDs), and may be disposed adjacent to, surrounding, and/or integrated with camera 1193, in any configuration that permits the camera to capture images of the surgical site. In some embodiments the illumination source 1194 may comprise a light guide and a source of illumination located elsewhere within or exterior to a surgical apparatus of which distal bulb 1100 is a part, by which light is conveyed from such exterior source to bulb 1100.

Figure 19:
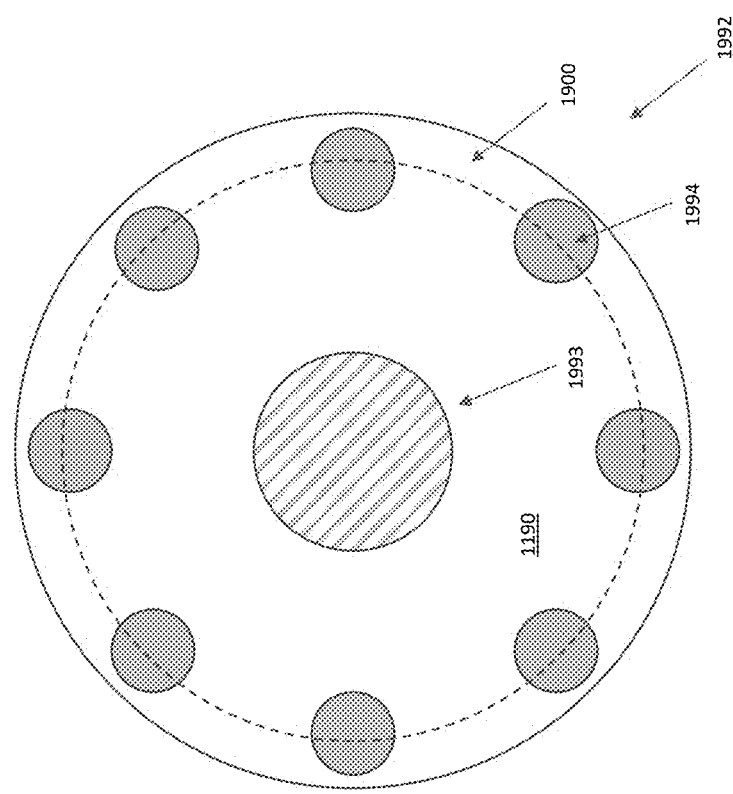
FIG. 19 illustrates an example of an integrated imaging system.

An example of imaging system 1192 is integrated imaging system 1992 in FIG. 19. Integrated Imaging system 1992 includes a body or housing 1990 on which a camera 1993 and a plurality of light sources 1994 (e.g., LEDs) are disposed along a virtual circle 1900 where the camera 1993 is disposed in the center of the virtual circle 1900. The light sources 1994 can be disposed or located in a counterbore (e.g., counterbore 1197 and/or 1530) of an imaging channel (e.g., imaging channel 1190 and/or 1520).

Imaging channel 1190 is open to the proximal face 1128 of the bulb, allowing electrical connection to be made to the camera 1193 and/or illumination source 1194, in order to provide power and control signals, and in some embodiments light from an exterior source, to and receive transmitted images from the imaging system. In a typical embodiment, such electrical connections pass through an opening in a gasket (e.g., valve gasket 124) to a channel in a port body, separate from the instrument channel in such port body, to reach power sources and other circuitry used with the imaging system 1192. The gasket between the port body and the bulb 1100 helps keep the imaging system 1192 fluidically isolated from the surgical site, thus avoiding electrical shorts and other malfunctions from contact of electrical equipment and connections with bodily or other fluids, and also avoiding the possibility of electrical signals being transmitted into the surgical site from the imaging system 1192 and causing unintended electrical stimulation of bodily tissue, which could be particularly dangerous during cardiac procedures. Fluidically isolating the imaging system 1192 also reduces the risk of infection during surgery by reducing the number of components exposed to the surgical site. In order for the gasket to form a good seal, the connecting rods press on the distal-facing surface 1127 of the flanged proximal portion 1121 of the bulb 1100, compressing the bulb 1100 against the gasket and the gasket against the distal end of the port body. The connecting rods are attached at their proximal ends to a mechanism that allows them to be pulled in the proximal direction, thus putting the connecting rods in tension, in order to provide a mechanical force on the distal-facing surface of the flanged portion 1121 of the bulb 1100 to keep the gasket seal tight. A tight seal is particular necessary to maintain the integrity of the seal when the surgical apparatus is subject to stresses, including bending stresses, during use while it is being manipulated by the surgeon inside the body of the patient, particularly when encountering hard or stiff bodily tissues of the patient.

As can be seen, bulb 1100 includes a first body 1200 and a second body 1210 extending from a proximal side 1202 of the first body 1200. The first body 1200 has a hemispherical or substantially hemispherical distal side 1204, which may be referred to as rounded distal portion 1126. A portion 1220 adjacent to hemispherical or substantially hemispherical distal side 1204 has a different curvature than hemispherical or substantially hemispherical distal side 1204, for example, to enlarge the diameter of the bulb 1100 while keeping the desired curvature and optical properties of the hemispherical or substantially hemispherical distal side 1204. The proximal side 1202 of the first body 1200 is planar or substantially planar. The second body 1210 includes a flange, which may be referred to as flanged proximal portion 1121, at or near the proximal side 1212 of the second body 1210. The flange defines the narrowed central portion 1123 in the distal portion 1214 of the second body 1210.

The instrument channel 1180 extends from the proximal side 1212 of the second body 1210 to the substantially hemispherical distal side 1204 of the first body 1200. The imaging channel 1190 extends from an aperture 1196 defined in the proximal side 1212 of the second body 1210 and terminates between the proximal and substantially hemispherical distal sides 1202, 1204, respectively, of the first body 1200.

Figures 12, 13:
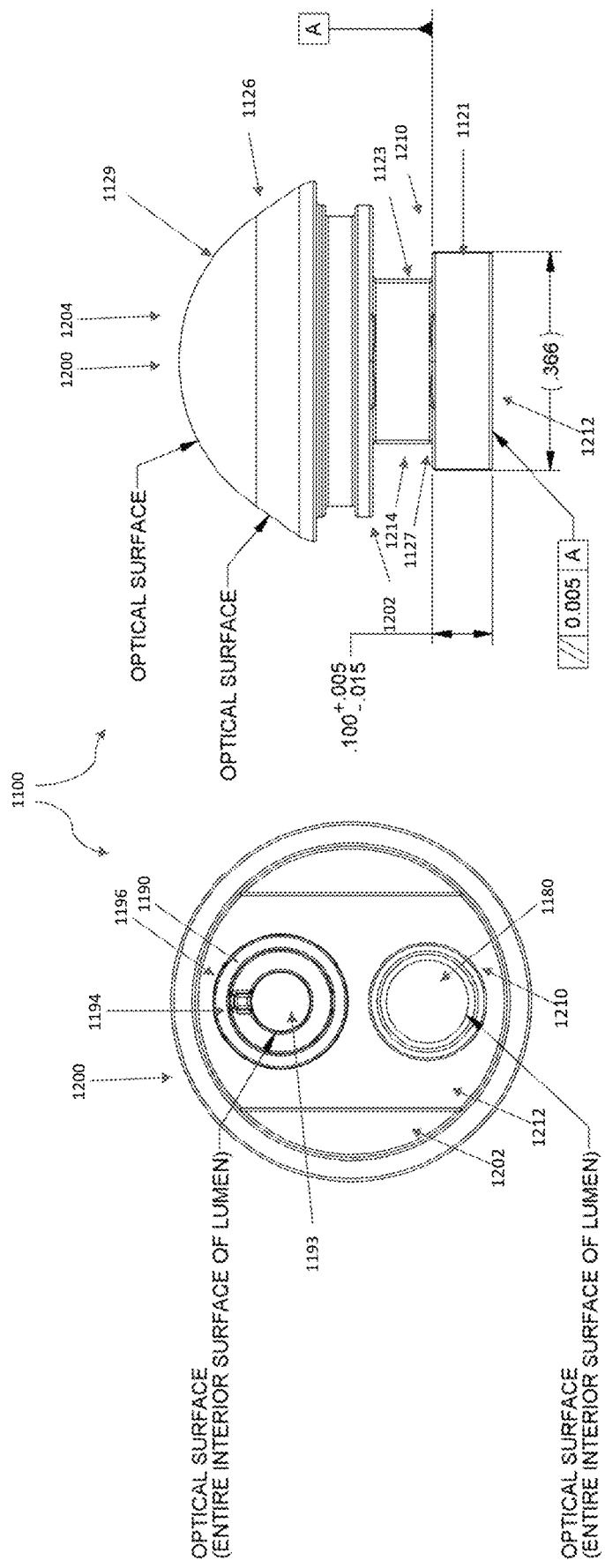
FIG. 12 is a rear (proximal) view of a bulb comprising a distal portion of the instrument port disclosed herein, according to one or more embodiments, with certain optical features shown.
FIG. 13 a side view of a bulb comprising a distal portion of the instrument port disclosed herein, according to one or more embodiments, with exemplary dimensions and certain optical and other features shown.

FIG. 12 shows a rear/proximal view of an exemplary bulb 1100, which may be the same as or similar to the bulb 1100 shown in FIGS. 11A-E, in greater detail, pointing out certain optical features of the bulb. FIG. 13 shows a top view of an exemplary bulb 1100, which may be similar to the bulb shown in FIGS. 11A-E, with certain optical features and exemplary dimensions shown. Note that the interior surfaces of both lumens, i.e. instrument channel 1180 and imaging system channel 1190, are optical surfaces, as is the exterior distal surface 1129 of the bulb 1100. Light from the illumination source 1192 passes through these surfaces and is refracted on the way to the site being imaged, and the light reflected from the site being imaged is refracted through these surfaces on the way to the camera 1193 where such light is captured as an image.

Figure 14:
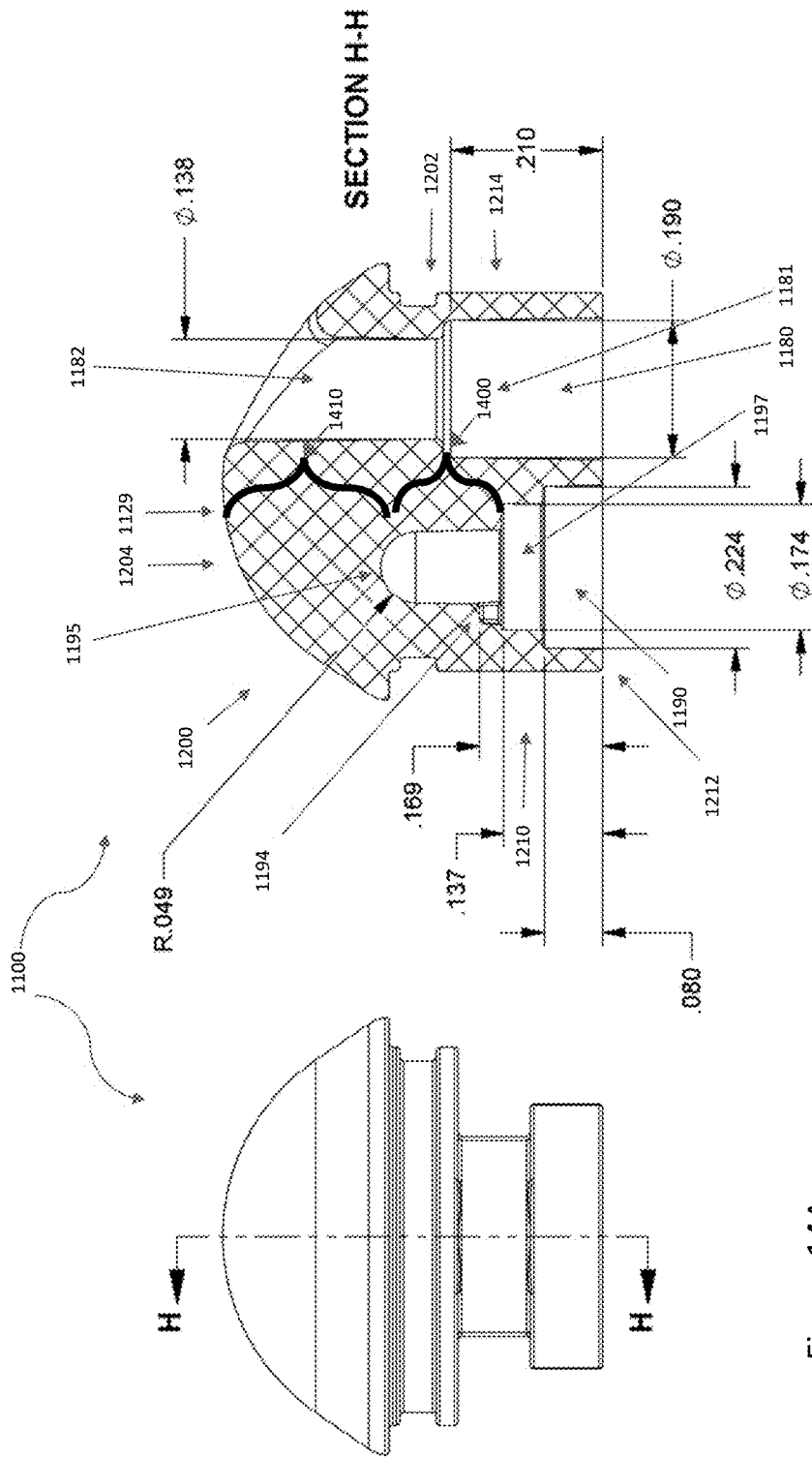
FIG. 14A is a side view of a bulb comprising a distal portion of the instrument port disclosed herein, according to one or more embodiments.
FIG. 14B is a sectional view of the bulb of FIG. 14A along the line H-H thereof, showing internal features of the bulb and exemplary dimensions.

FIG. 14A shows the top view of the bulb 1100 as in FIG. 13, and FIG. 14B shows a sectional view of such bulb along the line H-H of FIG. 14A, allowing certain interior features of the bulb, including channels 1180 and 1190, to be seen, with exemplary dimensions shown. Imaging channel 1190 has a hemispherical or a substantially hemispherical distal end 1195 and a counterbore 1197 at or near the proximal side 1202 of the first body 1200. In other embodiments, the counterbore 1197 is disposed between (e.g., in approximately the center of or other location) the proximal side 1202 of the first body 1200 and the distal end 1195 of the imaging channel 1190. In some embodiments, the light source 1193 can be disposed in the counterbore 1197 such that the illumination source 1194 is located outside of the main imaging channel 1190. The illumination source 1194 can be integrated with the camera 1193, for example the illumination source 1194 can be disposed radially (e.g., along a virtual circle where the camera 1193 is in the center of the virtual circle) about the camera. Instrument channel 1180 is optionally tapered, becoming narrower between its proximal portion 1181 and its distal portion 1182.

The distance 1400 from the distal end 1195 of the imaging channel 1190 to the counterbore 1197 and the distance 1410 from the distal end 1195 of the imaging channel 1190 to the distal surface 1129 of the bulb 1100 are selected to reduce distortion of the image viewed by camera 1193, to create the desired field of view of the tissue as viewed through camera 1193, and to reduce reflection and/or shadowing of light emitted by illumination source 1194 (e.g., at or near the center of the field of view of camera 1193).

The imaging system, such as imaging system 1192, is designed to assist the surgeon performing a procedure by providing images in real time of the surgical site, the surgical instrument or instruments deployed at the surgical site, and the interaction of such instrument or instruments with the patient's tissue. To be effective the illumination source 1194, e.g. LEDs, of the imaging system 1192 can provide sufficient illumination of all parts of the site to be imaged, and the camera 1193 can capture in-focus images of the surgical site with a minimum of distortion. Light rays from the illumination source 1194 as they travel to the surgical site, and as they are reflected back to the camera 1193, are subject to reflection and refraction at the interfaces between the material of the bulb 1100 and, respectively, the air inside the imaging channel 1190, bodily fluids inside the instrument channel 1180, and bodily fluids outside the distal surface 1129 of the bulb 1100.

Figure 15:
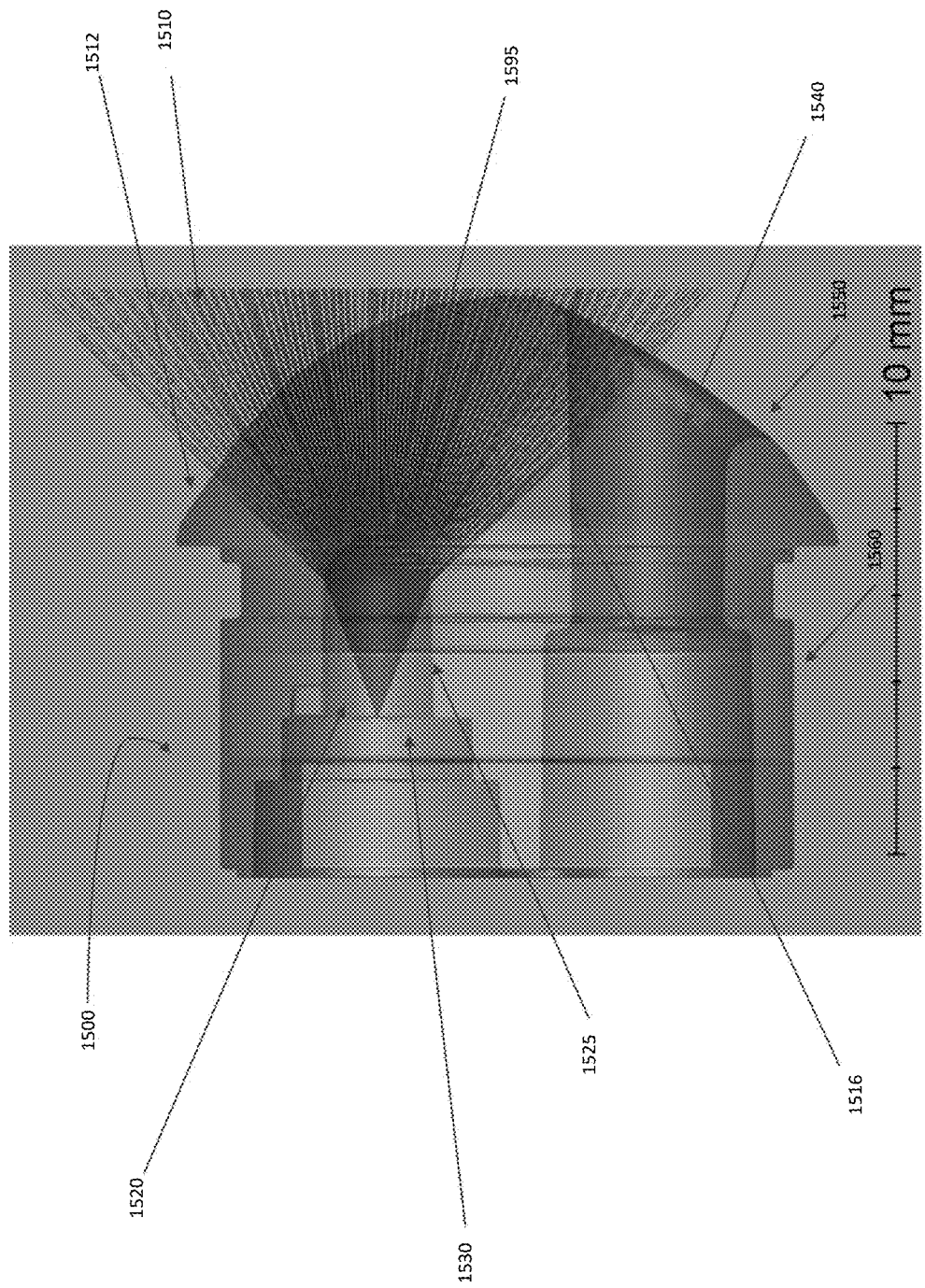
FIG. 15 is a side view of an exemplary bulb showing the paths of light rays from outside the distal end of the bulb to the bulb's camera.

As such, the size and shape of the optical surfaces represented by these interfaces must be designed with these goals in mind. For example, the location of the illumination source 1194 (and the location of counterbore 1197) and the cross-sectional diameter or width of the imaging channel 1190 can be selected to reduce the reflection of light, emitted from the illumination source 1194, within the imaging channel 1190. In some embodiments, the inner cross-sectional diameter or width of the imaging channel 1190 is about 2.5 mm. As used herein, "about" means plus or minus 10% of the relevant value. In another example, the substantially hemispherical distal end 1195 of the imaging channel 1190 is configured to refract light passing out of the imaging channel 1190 towards the instrument channel 1180 (e.g., as illustrated in FIG. 15, which refers to these channels as imaging channel 1520 and instrument channel 1540, respectively). The substantially hemispherical distal end 1195 of the imaging channel 1190 can also eliminate and/or substantially eliminate total internal reflection of light, emitted from the illumination source 1194, at a wall or interface of the instrument channel 1180. The substantially hemispherical distal end 1195 of the imaging channel 1190 can also have a negative power to increase the field of view of the camera 1193. One or more of the foregoing can create a substantially uniform image path within the field of view of the camera 1193. For example, one or more of the foregoing can cause light emitted from the illumination source 1194 to be substantially uniform distally from the first body 1210 (e.g., as illustrated in FIG. 15).

Furthermore, because blood and other bodily fluids may be opaque to some wavelengths of light from the illumination source 1194, the bulb 1100 and the camera 1193 are configured and located such that the focal distance of the camera 1193 is approximately equal to the distance from the camera 1193 to the distal surface 1129 of the bulb 1100, thus allowing the camera 1193 to focus on bodily tissue that is adjacent to or touching the distal surface 1129.

FIG. 15 illustrates the paths of light rays 1510 from a surgical site toward the camera of an exemplary bulb 1500 embodying the invention disclosed herein. Bulb 1500 can be the same as or similar to bulb 1100 and/or bulb 120. Bulb 1500 includes first and second bodies 1550, 1560, which can be the same as or substantially the same as first and second bodies 1200, 1210, respectively. Bulb 1500 includes an imaging channel 1520 having a counterbore 1530 to receive an illumination or light source, such that the illumination source is located outside of the main imaging channel 1520. In operation, light rays 1510 emitted from the illumination source in counterbore 1530 pass through a substantially hemispherical distal end 1195 of the imaging channel 1520 in the same or similar way as described above with respect to substantially hemispherical distal end 1195.

In FIG. 15, the location of the illumination source (and the location of counterbore 1530) and the cross-sectional diameter or width of the imaging channel 1520 are selected to reduce the reflection of light 1510, emitted from the illumination source, within the imaging channel 1520. In some embodiments, the inner cross-sectional diameter or width of the imaging channel 1520 is about 2.5 mm. As illustrated, the substantially hemispherical distal end 1595 of the imaging channel 1520 is configured to refract light 1510 passing out of the imaging channel 1520 towards the instrument channel 1540. The substantially hemispherical distal end 1595 of the imaging channel 1520 eliminates and/or substantially eliminates total internal reflection of light 1510, emitted from the illumination source, at a wall or interface 1525 of the instrument channel 1520. The substantially hemispherical distal end 1595 of the imaging channel 1520 has a negative power to increase the field of view of the camera, which can be disposed in the instrument channel 1520 in the same cross-sectional plane as the counterbore 1530. One or more of the foregoing can create a substantially uniform image path within the field of view of the camera (e.g., as represented by light 1510). For example, one or more of the foregoing can cause light 1510 emitted from the illumination source to be substantially uniform distally from the first body 1550, which can be the same as or substantially the same as first body 1550.

FIG. 16 shows a simulated distribution 1600 of illumination outside the distal end of the bulb of FIG. 15, such illumination coming from the LEDs or other illumination source of the imaging system of the bulb 1500.

For the bulb to be effective in surgical procedures, it is desirable that the overall diameter of the bulb not exceed 15-16 mm, including 15.1 mm, 15.2 mm, 15.3 mm, 15.4 mm, 15.5 mm, 15.6 mm, 15.7 mm, 15.8 mm, and/or 15.9 mm. Thus the sizes of both the instrument channel and the imaging system cavity or channel are constrained to fit within this overall diameter, and of course the instrument channel must be sufficiently wide to permit surgical instruments to pass through. A larger diameter for the imaging system cavity results in less curvature of the cavity's surface, which results in less distortion of the image received by the camera. With too much curvature, images will appear significantly out of focus everywhere but near the center of the camera's field of view. However, a larger cavity, with less curvature, increases reflection of the light from the LEDs, resulting in "dark spots," or areas of the surgical site that are insufficiently illuminated by the LEDs. Thus, there is a tradeoff between the need for sufficient, uniform illumination, and the need to reduce distortion of the images captured by the camera. It has been found that an illumination system cavity or channel diameter on the order of 2.5 mm represents a good compromise between these considerations.

Figures 17, 18:
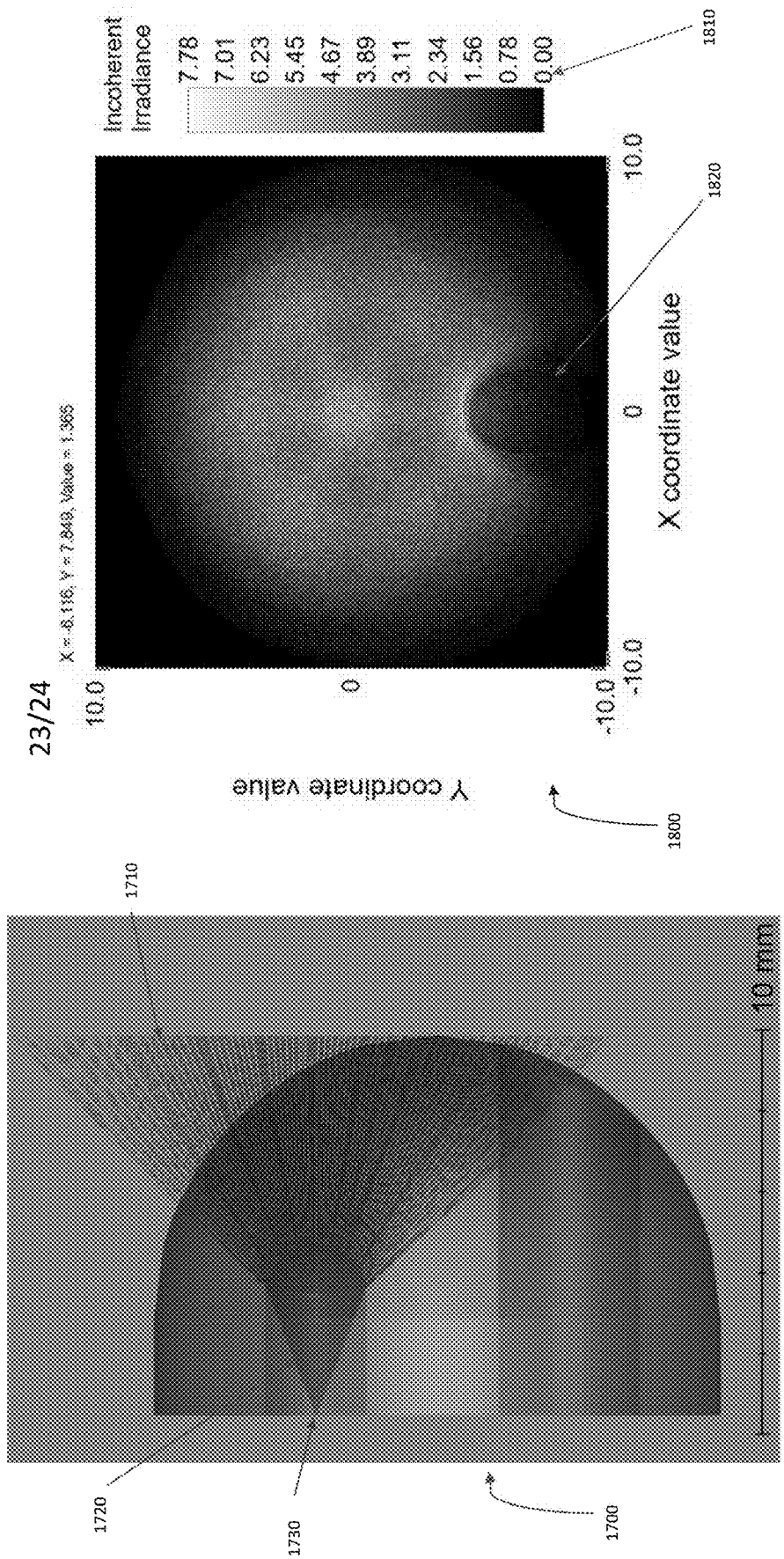
FIG. 17 is a simplified side view of an exemplary bulb showing the paths of light rays from outside the distal end of the bulb to the bulb's camera.
FIG. 18 is a simulated illumination distribution outside the distal end of the bulb of FIG. 17.

FIG. 17 depicts a simplified side view of a distal portion of an exemplary bulb 1700 with a 2.5 mm illumination channel 1720, showing the path of light rays 1710 reaching camera 1730 and/or the path of light rays 1710 emitted by a light source. FIG. 18 depicts a plot 1800 showing a simulated distribution of illumination, as represented by scale 1810, at the surgical site over the camera's field of view, with the bulb design and dimensions of FIG. 17, where it can be seen that the illumination reaches the entire field of view. Instrument channel 1820 can be seen at the bottom-center of the plot 1800.

The apparatus with instrument ports and distal bulb tip described herein can be used to perform cardiac procedures, such as beating heart cardiac procedures. Examples of cardiac procedures that can be carried out by the instrument ports described herein include closure of heart defects, such as septal defects, heart valve annuloplasty, and other procedures. The imaging capabilities provided by the instrument ports described here provide high quality imaging of the surgical procedure, thereby enabling complex surgical procedures to be carried out with a high degree of precision.

In the foregoing specification, certain aspects have been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention.

What is claimed is:
1. An apparatus comprising:
a housing having a surface for a user to hold the apparatus;
a shaft that extends from the housing, the shaft including a port body having first and second channels;
an optical bulb disposed at a distal end of the shaft, the optical bulb comprising:
a first body having a substantially hemispherical distal side;

a second body extending from a proximal side of the first body, the second body including a mechanical connection point disposed at or near a proximal side of the second body;

an instrument channel extending from the proximal side of the second body to the substantially hemispherical distal side of the first body, the instrument channel aligned with the first channel in the port body; and an imaging channel that extends from an aperture defined in the proximal side of the second body, the imaging channel terminating at a distal end of the imaging channel between the proximal and substantially hemispherical distal sides of the first body, defining a continuous enclosed space from the aperture defined in the proximal side of the second body to the distal end of the imaging channel, and aligned with the second channel in the port body, wherein the distal end of the imaging channel is substantially hemispherical, wherein the first body is configured and arranged to provide a substantially uniform image path within a field of view of a camera disposed in the imaging channel, and wherein the substantially hemispherical distal end of the imaging channel has a negative power that increases the field of view of the camera.

2. The apparatus of claim 1, wherein the substantially hemispherical distal end of the imaging channel is configured to refract light passing out of the imaging channel towards the instrument channel.

3. The apparatus of claim 2, wherein the substantially hemispherical distal end of the imaging channel eliminates a total internal reflection of light at a wall of the instrument channel.

4. The apparatus of claim 3, wherein a light source for the camera is located outside of the imaging channel.

5. The apparatus of claim 4, wherein the light source is disposed in a counterbore of the imaging channel.

6. The apparatus of claim 4, wherein the light source is integrated with the camera.

7. The apparatus of claim 4, wherein the location of the light source and an inner cross-sectional diameter of the imaging channel are selected to reduce a reflection of light within the imaging channel, the light emitted by the light source.

8. The apparatus of claim 7, wherein the inner cross-sectional diameter is about 2.5 mm.

9. The apparatus of claim 7, wherein the light emitted by the light source is substantially uniform distally from the first body within the field of view of the camera.

10. The apparatus of claim 4, wherein the light source comprises a plurality of light-emitting elements, each light-emitting element disposed along a common virtual circle, wherein the camera is disposed at a center of the common virtual circle.

11. The apparatus of claim 10, wherein the light-emitting elements comprise light emitting diodes.

12. The apparatus of claim 1, wherein the first and second bodies comprise a same material.

13. The apparatus of claim 12, wherein the same material comprises an acrylic thermoplastic.

14. The apparatus of claim 1, wherein the mechanical connection point comprises a flange.

* * * * *